(12) United States Patent
Dube et al.

(10) Patent No.: US 11,560,353 B2
(45) Date of Patent: *Jan. 24, 2023

(54) TRICYANOHEXANE PURIFICATION METHODS

(71) Applicant: Ascend Performance Materials Operations LLC, Houston, TX (US)

(72) Inventors: Sanjay Dube, Madison, AL (US); Benjamin Haseltine, Houston, TX (US); Jefferson Thomas Ebert, League City, TX (US); Darrick Elmore, Pensacola, FL (US)

(73) Assignee: Ascend Performance Materials Operations LLC, Houston, TX (US)

( * ) Notice: Subject to any disclaimer, the term of this patent is extended or adjusted under 35 U.S.C. 154(b) by 72 days.

This patent is subject to a terminal disclaimer.

(21) Appl. No.: 17/138,591

(22) Filed: Dec. 30, 2020

(65) Prior Publication Data

US 2021/0198186 A1 Jul. 1, 2021

Related U.S. Application Data

(60) Provisional application No. 62/955,086, filed on Dec. 30, 2019.

(51) Int. Cl.
*C07C 253/34* (2006.01)
(52) U.S. Cl.
CPC .................. *C07C 253/34* (2013.01)
(58) Field of Classification Search
None
See application file for complete search history.

(56) References Cited

U.S. PATENT DOCUMENTS

| 3,451,900 A | 6/1969 | Gey et al. |
| 3,844,911 A | 10/1974 | Ruehlen |

(Continued)

FOREIGN PATENT DOCUMENTS

| JP | 2003192631 A | 7/2003 |
| TW | 201728620 A | 8/2017 |

OTHER PUBLICATIONS

Costello (Distillation Part 2—Reboilers, originally published on Nov. 24, 2016 and downloaded from https://rccostello.com/wordpress/boilers/distillation-part-2-reboilers/ on May 5, 2022). (Year: 2016).*

*Primary Examiner* — Amy C Bonaparte
(74) *Attorney, Agent, or Firm* — Cozen O'Connor

(57) ABSTRACT

The present disclosure relates generally to processes for recovering tricyanohexane (TCH) via purification of by-product or co-product streams of adiponitrile production. In particular, the present disclosure relates to a process for purifying tricyanohexane (TCH), the process having the steps of (a) separating an adiponitrile process stream comprising adiponitrile and TCH to form a first overhead lights stream comprising low-boiling components and high-boiling components and a first bottoms heavies stream comprising high-boiling components and solid impurities; and (b) separating the first overhead lights stream in a distillation column to form a second overhead lights stream comprising low-boiling components, a second bottoms heavies stream comprising high-boiling components, and a TCH stream comprising TCH and less than 10 wt. % impurities; wherein the distillation column is a low pressure distillation column.

18 Claims, 5 Drawing Sheets

(56) References Cited

U.S. PATENT DOCUMENTS

| | | |
|---|---|---|
| 6,599,398 B1 | 7/2003 | Ostermaier et al. |
| 7,262,256 B2 | 8/2007 | Date et al. |
| 2005/0010021 A1* | 1/2005 | Date ................. C08G 59/4207 528/365 |
| 2021/0155579 A1* | 5/2021 | Boehlow ............... C07C 253/34 |

* cited by examiner

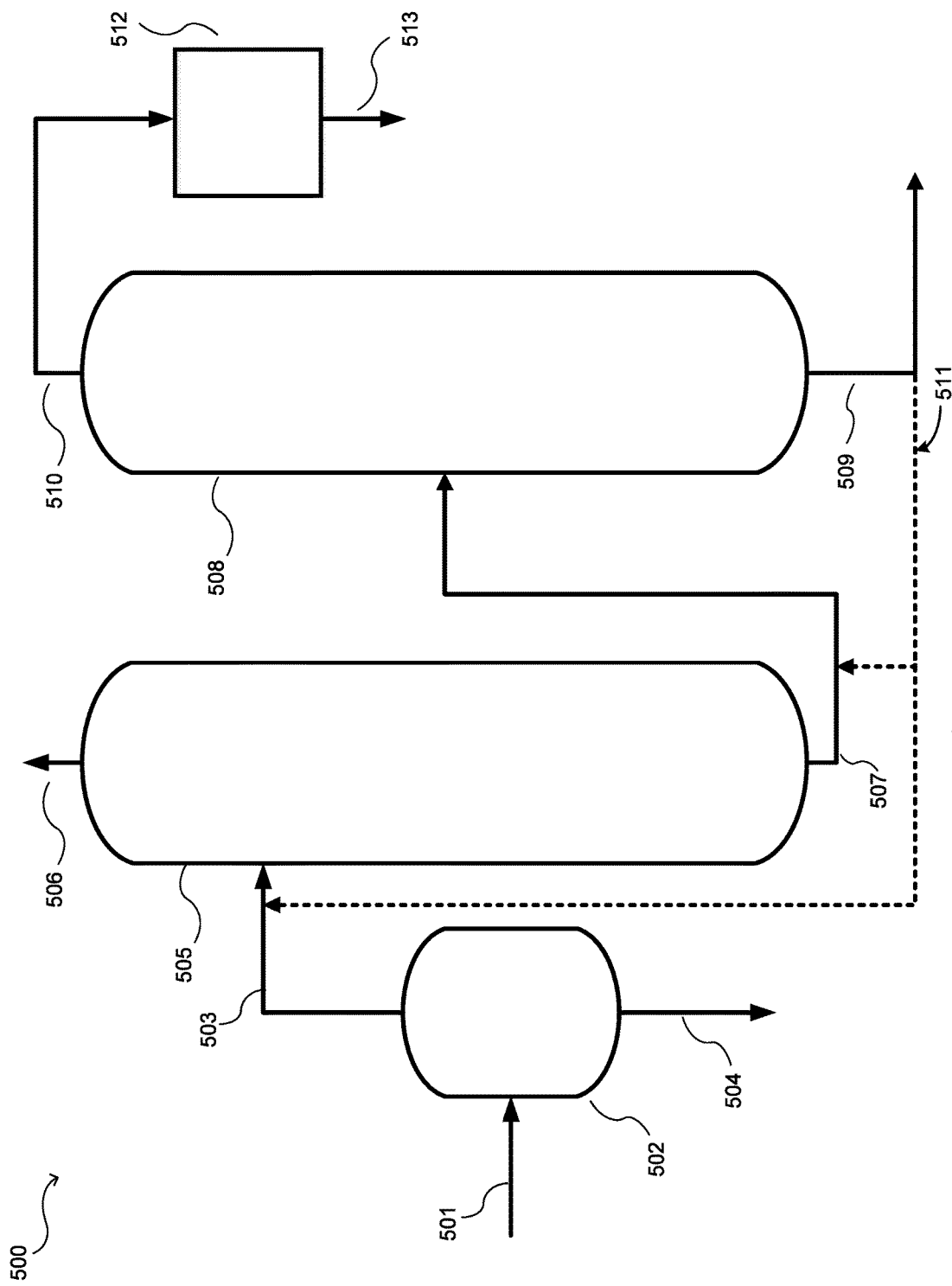

US 11,560,353 B2

TRICYANOHEXANE PURIFICATION METHODS

REFERENCE TO RELATED APPLICATION

This application claims priority to U.S. Provisional Application No. 62/955,086, filed on Dec. 30, 2019, which is incorporated herein by reference.

FIELD

The present disclosure relates generally to production of tricyanohexane (TCH) via purification of co-product streams of industrial processes. More specifically, the present disclosure relates to processes for recovering TCH present in streams resulting from the production of adiponitrile.

BACKGROUND

Cyanocarbons, e.g., organic compounds having cyano functional groups, are known and are widely used in various applications. Many of these compounds, including acrylonitrile and adiponitrile (ADN), are used as monomers to prepare various polymers, such as nylon, polyacrylonitrile, or acrylonitrile butadiene styrene. Adiponitrile, in particular, can be hydrogenated to 1,6-diaminohexane (hexamethylenediamine (HMD)) for the production of nylon-6,6. Several processes for producing cyanocarbons are known in the art. For example, one conventional adiponitrile production path utilizes the electrohydrodimerization of acrylonitrile, as described in U.S. Pat. No. 3,844,911.

This and other production methods often yield streams comprising small amounts of desirable co-products. For example, some of the conventional streams of adiponitrile production processes may contain small but not insignificant amounts of residual adiponitrile. Typically, separation of these streams has been inefficient and has not been able to effectively capture these amounts of adiponitrile. As a result, the streams are treated as waste streams, e.g., burned, which results in an outright loss of these co-products. Accordingly, valuable adiponitrile goes uncaptured.

Some ADN separation/purification processes are known. However, these processes generally relate to purification of a crude adiponitrile product stream, which comprise higher concentrations of adiponitrile.

For example, U.S. Pat. No. 3,451,900 relates to a method for the production of pure adiponitrile from a reaction product containing adiponitrile, cyclopentanone, 2-cyancyclopenten-(1)-yl-amine and other components higher boiling than adiponitrile wherein cyclopentanone and 2-cyancyclopenten-(1)-yl-amine are distilled from the adiponitrile, the improvement which comprises subjecting the reaction product to a distillation for separation into a distillate comprising adiponitrile and all lower boiling components and a residue comprising components higher boiling than adiponitrile, and thereafter submitting said distillate to a multistage vacuum distillation process for separating the lower boiling impurities from the adiponitrile.

Also, U.S. Pat. No. 6,599,398 relates to a process for the recovery of a purified adiponitrile from a mixture of adiponitrile, aminocapronitrile and hexamethylenediamine, utilizing two sequential distillations: (1) a first distillation in which the mixture is distilled in a distillation column at a head pressure that causes at least 7% of the ADN to go into the distillate, along with bishexamethylenetriamine (BHMT) and 2-cyanocyclopentylideneimine (CPI), and (2) a second distillation in which the distillate from the first distillation is distilled in a second distillation column at a head pressure sufficient to cause minimum-temperature azeotropy between adiponitrile and BHMT, thereby allowing the majority of the BHMT and CPI to be removed from the second distillation as distillate, and adiponitrile, substantially free of both BHMT and CPI, to be removed as bottoms.

Even in view of the known technology, the need exists for processes that can effectively recover amounts of residual adiponitrile from lower adiponitrile content cyanocarbon production process streams, which result in significant improvements in overall production efficiency.

SUMMARY

The present disclosure provides processes for recovering TCH from industrial process streams, especially process streams from the production of adiponitrile. In one aspect, the disclosure provides a process for purifying tricyanohexane (TCH), the process comprising: a) separating an adiponitrile process stream comprising adiponitrile and TCH to form a first overhead lights stream comprising low-boiling components and high-boiling components and a first bottoms heavies stream comprising high-boiling components and solid impurities; and b) separating the first overhead lights stream in one or more distillation columns to form a second overhead lights stream comprising low-boiling components, a second bottoms heavies stream comprising high-boiling components, and a TCH stream comprising TCH and less than 10 wt. % impurities; wherein the distillation column is a low pressure distillation column. In some cases, the low pressure distillation column is operated under vacuum. In some cases, the low pressure distillation column is operated with a column top pressure less than 100 mm Hg. In some cases, the low pressure distillation column is operated with a column bottom pressure less than 100 mm Hg. In some cases, the distillation column comprises a reboiler and the reboiler is operated at a temperature greater than 250° C. In some cases, the distillation column comprises a reboiler and the reboiler utilizes a hot oil system In some cases, step a) comprises flashing the adiponitrile process stream, treating the adiponitrile process stream in a wiped film evaporator, and/or treating the adiponitrile process stream in a falling film evaporator. In some cases, step a) is carried out at a temperature of at least 250° C. In some cases, the TCH stream comprises less than 1 wt. % impurities. In some cases, the first overhead lights stream comprises from 0 wt. % to 20 wt. % heavies. In some cases, the process further comprises recycling at least a portion of the second bottoms heavies stream, optionally comprising from 0 wt. % to 40 wt. % high-boiling components. In some cases, step b) further comprises: separating the first overhead lights stream in a first distillation column to form the second overhead lights stream and the second bottoms heavies stream; and separating the second bottoms heavies stream in a second distillation column to form a third bottoms heavies stream and a third overhead TCH stream. In some of these cases, the process may further comprise recycling at least a portion of the third bottoms heavies stream to the second bottoms heavies stream and/or to the first overhead lights stream. In some cases, the process further comprises a treating step of treating the TCH stream to form a purified TCH stream. The treating step may comprise nitrogen stripping or treating with a molecular sieve. The purified TCH stream may comprise less than 0.1 wt. % impurities, less than 20 ppm water, and/or less than 5 ppm metals. In some cases, the adiponitrile process stream is a co-product stream produced by an adiponitrile production and/or an adiponitrile purification process. In some cases, the first bottoms heavies stream and/or the second overhead lights stream is recycled to the adiponitrile production and/or the adiponitrile purification process.

In another aspect, the present disclosure provides a process for purifying TCH, the process comprising: a) separating an adiponitrile process stream comprising adiponitrile and TCH to form a first overhead lights stream comprising low-boiling components and high-boiling components, and a first bottoms heavies stream comprising high-boiling components and solid impurities; b) separating the first overhead lights stream to form a second overhead lights stream comprising low-boiling components, and a second bottoms heavies stream comprising TCH and heavies; c) distilling the second bottoms heavies stream to form a third overhead lights stream comprising TCH and less than 5 wt,% impurities, and a third bottoms heavies stream comprising heavies; wherein step b) or step c) comprises distilling in a low pressure distillation column. In some cases, the low pressure distillation column comprises a reboiler and the reboiler is operated at a temperature greater than 250° C.

In another aspect, the present disclosure provides a process for purifying TCH, the process comprising a) separating an adiponitrile process stream comprising adiponitrile and TCH to form a first overhead lights stream comprising low-boiling components and high-boiling components, and a first bottoms heavies stream comprising high-boiling components and solid impurities; b) distilling the first overhead lights stream to form a second overhead lights stream comprising low-boiling components, a second bottoms heavies stream comprising heavies, and a side draw comprising TCH and lights; c) separating the side draw in a second flash vessel to form a third bottoms heavies stream comprising TCH and less than 5 wt. % impurities wherein step b) or step c) comprises distilling in a low pressure distillation column. In some cases, the low pressure distillation column comprises a reboiler, and the reboiler is operated at a temperature greater than 250° C.

In another aspect, the present disclosure provides a process for purifying TCH, the process comprising: a) separating an adiponitrile process stream to form a first overhead lights stream comprising low-boiling components and high-boiling components, and a first bottoms heavies stream comprising high-boiling components and solid impurities; b) distilling the first overhead lights stream to form a second overhead lights stream comprising low-boiling components, and a second bottoms heavies stream comprising TCH and heavies; c) distilling the second bottoms heavies stream to form a third distillate comprising TCH and impurities, and a third bottoms heavies stream comprising heavies; and d) distilling the third distillate to form a fourth overhead lights stream comprising low-boiling components, and a fourth bottoms heavies stream comprising TCH and less than 5 wt. % impurities wherein the step b), step c), or step d) comprises distilling in a low pressure distillation column. In some cases, the low pressure distillation column comprises a reboiler, and the reboiler is operated at a temperature greater than 250° C.

In another aspect, the present disclosure provides a process for purifying TCH, the process comprising: a) separating an adiponitrile process stream to form a first overhead lights stream comprising low-boiling components and high-boiling components, and a first bottoms heavies stream comprising high-boiling components and solid impurities; b) distilling the first overhead lights stream to form a second overhead lights stream comprising low-boiling components, and a second bottoms heavies stream comprising TCH and heavies; c) distilling the second bottoms heavies stream to form a third distillate comprising TCH and impurities, and a third bottoms heavies stream comprising heavies; and d) separating the third distillate in a second flash vessel to form a fourth overhead lights stream comprising low-boiling components, and a fourth bottoms heavies stream comprising TCH and less than 5 wt. % impurities wherein step b), step c), or step d) comprises distilling in a low pressure distillation column. In some cases, the low pressure distillation column comprises a reboiler, and the reboiler is operated at a temperature greater than 250° C.

BRIEF DESCRIPTION OF THE DRAWINGS

The disclosure is described in detail below with reference to the appended drawings, wherein like numerals designate similar parts.

FIG. 5 depicts a schematic overview of another embodiment of the process for producing an intermediate adiponitrile stream.

DETAILED DESCRIPTION

Introduction

Figure 1:
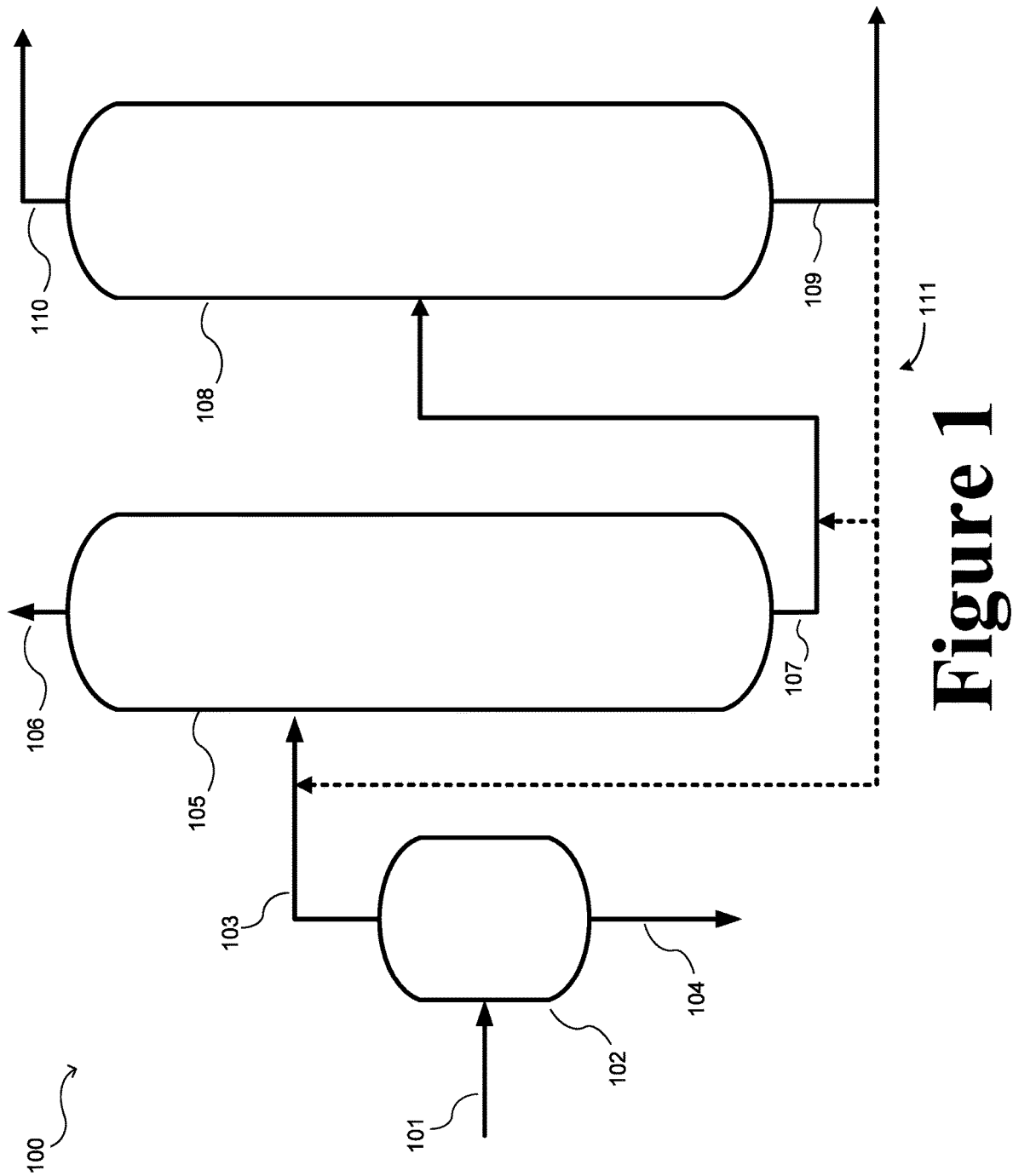
FIG. 1 depicts a schematic overview of an embodiment of the process for producing an intermediate adiponitrile stream.

As noted above, many conventional cyanocarbon production process steams contain (lower) amounts of desirable co-products, such as adiponitrile and TCH, e.g., as 1,3,6-tricyanohexane and/or 1,2,6-tricyanohexane. In conventional processes, the separation and/or recovery of these amounts of adiponitrile and/or TCH has proven to be ineffective and impractical. Conventional processes for separation and/or recovery of TCH, for example, rely on differing boiling points of components. Because TCH and other high-boiling components present in cyanocarbon production streams have high boiling points, e.g., boiling points greater than 300° C., greater than 350° C., or greater than 400° C., conventional processes rely on extremely high temperatures to boil the streams.

It has been discovered, however, that certain components in cyanocarbon production process streams are prone to decomposition during conventional separation processes. The decomposition products have been found to limit the capability of meeting commercially desirable purity of TCH. Conventional TCH recovery processes do not account for this decomposition and, as a result, require additional purification steps, causing lower efficiencies.

Furthermore, the inventors have now found that the temperature to which process streams are exposed affects decomposition and that decomposition can be controlled, e.g., reduced or eliminated, by controlling temperatures. In particular, certain high-boiling components are prone to decomposition into impurities having both higher boiling points and lower boiling points. Prolonged exposure to high pressures temperatures contributes to the decomposition of high-boiling components, and as temperatures increase, rates of decomposition increase. In order to reduce the temperature, the present inventors have discovered special operation parameters for the process, described herein, that efficiently separate and purify TCH and mitigate or eliminate decomposition. In particular, the inventors have found that low pressure column operation, optionally in combination with high reboiler operating temperature, provides for unexpected separation efficiencies. It is postulated that higher reboiler temperatures, while leading to decomposition, may contribute to effective separation of other components. Surprisingly, it has been found that the low pressure column operation significantly mitigates any detrimental factors that may arise with high temperature reboiler operations, e.g., decomposition. Thus, the combination of the low pressure column operation and high reboiler operating temperature has been found to provide effective separation of some co-products, while unexpectedly limiting decomposition product formation.

Traditional purification schemes have focused on process streams that do not address decomposition of components and the effects thereof on separation efficiency. Typically, the purification schemes have not focused on process streams with appreciable amounts of high-boiling components, which contribute to high temperatures and thereby decomposition. For example, traditional purification schemes have not focused on separation and/or purification of process streams comprising appreciable amounts of TCH. As a result, these purification schemes have proven to be ineffective and impractical for use in separating and/or purifying process streams that do comprise high-boiling components. Because of the failure to address decomposition, traditional schemes provide little or no guidance with regard to the process streams described herein.

In some cases, the present disclosure relates to processes for purifying TCH. The processes comprise the step of separating an adiponitrile process stream to form a first overhead lights stream and a first bottoms heavies stream. The adiponitrile process stream comprises adiponitrile, and in some instances the adiponitrile process stream has a low adiponitrile content, e.g., less than 50 wt. % adiponitrile, as compared to traditional adiponitrile process stream. The adiponitrile process stream may further comprise TCH (additional compositional information of the adiponitrile process stream is provided below). The first overhead lights stream comprises low-boiling components, e.g., components having a boiling point lower than TCH. The first bottoms heavies stream comprises high-boiling components, e.g., components having a boiling point higher than TCH, and solid impurities.

The processes also comprise the step of separating the first overhead lights stream in a distillation column to form a second overhead lights stream, a second bottoms heavies stream, and a TCH stream. The second overhead lights stream comprises low-boiling components. The second bottoms heavies stream comprises high-boiling components. The TCH stream comprises TCH and less than 10 wt. % impurities.

Importantly, the distillation column may be a low pressure distillation column. As one example, the low pressure distillation column may be operated under vacuum. As another example, the low pressure distillation column is operated with a column top pressure less than 100 mm Hg and/or is operated with a column bottom pressure less than 100 mm Hg. The inventors have found that by conducting the separation, the column temperature can be reduced, which surprisingly provides for improved efficiency of the separation, e.g., by reducing or eliminating decomposition.

Importantly, the distillation column may comprise a high temperature reboiler. For example, the distillation column may comprise a reboiler that operates at temperatures greater than 250° C. To operate at such high temperatures, the reboiler may utilize special equipment. As one example, the distillation column comprises a reboiler that operates at temperatures greater than 250° C. and that utilizes a hot oil system.

The separations of the disclosed processes are effective and take into consideration other co-products, e.g., adiponitrile, which can also be separated and recovered. The present inventors have found that consideration of adiponitrile in TCH purification processes is also important, as adiponitrile has been found to decompose at high temperatures. The traditional schemes have not been found to effectively capture both adiponitrile and TCH.

The first separating step may vary but will typically lead to the aforementioned first overhead lights stream and will typically separate any solid impurities into the first bottom heavies stream. In some cases, the first separating step of the processes comprises flashing the adiponitrile process stream. In some cases, the first separating step comprises treating the adiponitrile process stream in a wiped film evaporator. In some cases, the first separating step comprises treating the adiponitrile process stream in a falling film evaporator.

In some cases, the second separating step of the adiponitrile process stream comprises separating the adiponitrile process stream in one or more distillation columns. As one example the second separating step may comprise separating the first overhead lights stream in a first distillation column to form the second overhead lights stream and the second bottoms heavies stream, and separating the second bottoms heavies stream in a second distillation column to form a third bottom heavies stream and a third overhead lights stream, which may be the TCH stream.

As another example, the second separating step may comprise separating the first overhead lights stream in a distillation column to form the second overhead lights stream, the second bottoms heavies stream, and a side draw, and separating the side draw in a flash vessel to form a third bottom heavies stream, which may be the TCH stream.

As another example, the second separating step may comprise separating the first overhead lights stream in a first distillation column to form the second overhead lights stream and the second bottoms heavies stream, separating the second bottoms heavies stream in a second distillation column to form a third overhead lights stream and a third bottom heavies stream, and separating the third overhead lights stream in a third distillation column to form a fourth overhead lights stream and a fourth bottoms heavies stream, which may be the TCH stream.

As another example, the second separating step may comprise separating the first overhead lights stream in a first distillation column to form the second overhead lights stream and the second bottoms heavies stream, separating the second bottoms heavies stream in a second distillation column to form a third overhead lights stream and a third bottom heavies stream, and separating the third overhead lights stream in a flash vessel to form a fourth overhead lights stream and a fourth bottoms heavies stream, which may be the TCH stream.

In each of these examples of the second separating step, each of the first distillation column, the second distillation column, and/or the third distillation column may be a low pressure distillation column. In each of these examples of the second separating step, each of the first distillation column the second distillation column, and/or the third distillation column may comprise a reboiler that operates at temperatures greater than 250° C. and/or that utilizes a hot oil system.

Adiponitrile Process Stream

As noted above, the adiponitrile process stream has a specific composition, which has surprisingly been found to separate efficiently when employing the disclosed processes. In particular, the adiponitrile process stream may comprise adiponitrile, TCH, high-boiling components, and low boiling components. Conventional separation processes have had difficulty in isolating the lower quantities of adiponitrile and/or TCH. In some embodiments, the adiponitrile process stream may be one or more process streams of another industrial chemical production process. For example, the adiponitrile process stream may comprise one or more process streams from different processes or systems, e.g., the production of adiponitrile, acrylonitrile, allyl cyanide, butyronitrile, polyacrylonitrile, polyamides, polyaramids, or combinations thereof. In a specific case, the adiponitrile process stream may be one or more process streams, purge streams, or flash tails from an adiponitrile production process. In some cases, streams from multiple processes may be combined to form the stream. In conventional processes, such adiponitrile-containing (and/or TCH-containing) streams are often treated as waste streams, e.g., vented or burned, and the valuable components are not recovered. By recovering adiponitrile and/or TCH from these streams, as described herein, the (residual) adiponitrile may be recovered and used or sold, thus increasing efficiency and profitability.

The adiponitrile process stream may comprise less than 40 wt % adiponitrile, e.g., less than 35 wt %, less than 30 wt %, less than wt 20%, less than 18 wt %, less than 15 wt %, less than 12 wt %, less than 10 wt %, or less than 5 wt %. In terms of ranges, the adiponitrile process stream may comprise from 0.1 wt % to 40 wt % adiponitrile, e.g., from 0.5 wt % to 30 wt %, from 1 wt % to 20 wt %, from 1 wt % to 18 wt %, from 1 wt % to 10 wt %, from 2 wt % to 15 wt %, from 3 wt % to 15 wt %, or from 5 wt % to 15 wt %. In terms of lower limits, the adiponitrile process stream may comprise greater than 0.1 wt % adiponitrile, e.g., greater than 0.3 wt %, greater than 0.5 wt %, greater than 0.7 wt %, greater than 1.0 wt %, greater than 1.5 wt %, greater than 2 wt %, or greater than 5 wt %.

In some embodiments, the adiponitrile process stream comprises less than 25 wt. % TCH, e.g., less than 20 wt. %, less than 18 wt. %, less than 15 wt. %, less than 12 wt. %, less than 10 wt. %, or less than 5 wt. %. In terms of ranges, the adiponitrile process stream may comprise from 0.1 wt. % to 25 wt. % TCH, from 0.5 wt. % to 23 wt. %, from 0.5 wt. % to 20 wt. %, from 1 wt. % to 15 wt. %, from 1.5 wt. % to 12 wt. %, or from 2 wt. % to 11 wt. %. In terms of lower limits, the adiponitrile process stream may comprise greater than 0.1 wt. % TCH, e.g., greater than 0.3 wt. %, greater than 0.5 wt. %, greater than 0.7 wt. %, greater than 1.0 wt. %, greater than 1.5 wt. %, greater than 2 wt. %, or greater than 5 wt. %.

In some embodiments, the adiponitrile process stream comprises higher amounts of TCH. In one embodiment, the adiponitrile process stream comprises TCH in an amount ranging from 0 wt. % to 90 wt. %, based on the total weight of the feed stream, e.g., from 0 wt. %, to 89 wt. %, from 0 wt. % to 88 wt. %, from 0 wt. % to 85 wt. %, from 0 wt. % to 84 wt. %, from 10 wt. % to 90 wt. %, from 10 wt. %, to 89 wt. %, from 10 wt. % to 88 wt. %, from 10 wt. % to 85 wt. %, from 10 wt. % to 84 wt. %, from 20 wt. % to 90 wt. %, from 20 wt. %, to 89 wt. %, from 20 wt. % to 88 wt. %, from 20 wt. % to 85 wt. %, from 20 wt. % to 84 wt. %, from 30 wt. % to 90 wt. %, from 30 wt. %, to 89 wt. %, from 30 wt. % to 88 wt. %, from 30 wt. % to 85 wt. %, from 30 wt. % to 84 wt. %, from 40 wt. % to 90 wt. %, from 40 wt. %, to 89 wt. %, from 40 wt. % to 88 wt. %, from 40 wt. % to 85 wt. %, from 40 wt. % to 84 wt. %, from 50 wt. % to 90 wt. %, from 50 wt. %, to 89 wt. %, from 50 wt. % to 88 wt. %, from 50 wt. % to 85 wt. %, from 70 wt % to 90 wt %, or from 50 wt. % to 84 wt. %. In terms of upper limits, the adiponitrile process stream may comprise less than 90 wt. % TCH, e.g., 89 wt. %., less than 88 wt. %, less than 85 wt. %, or less than 84 wt. %, In terms of lower limits, the adiponitrile process stream may comprise greater than 0 wt. % TCH, e.g., greater than 10 wt. %, greater than 20 wt. %, greater than 30 wt. %, greater than 40 wt. %, greater than 50 wt %, or greater than 60 wt %, or greater than 70 wt %.

In some cases, the adiponitrile process stream also comprises low-boiling components. Generally, the low-boiling components are impurities having relatively low boiling points. For example, each of the low-boiling components may have a boiling point of less than 415° C. at atmospheric pressure, e.g., less than 410° C., less than 400° C., less than 395° C., or less than 390° C. Examples of low-boiling components that may be present in the adiponitrile process stream include various cyanocarbons, e.g., acrylonitrile, propionitrile, hydroxypropionitrile, monocyanoethyl propylamine, succinonitrile, methylglutaronitrile, adiponitrile, 2-cyanocyclopentylidenimine, bis-2-cyanoethyl ether, di(2-cyanoethyl) amine, di-2-cyanoethyl propylamine, cyanovaleramide and combinations thereof.

In one embodiment, the adiponitrile process stream comprises low-boiling components in an amount ranging from 0 wt. % to 70 wt. %, e.g., from 0 wt. %, to 65 wt. %, from 0 wt. % to 60 wt. %, from 0 wt. % to 55 wt. %, from 0 wt. % to 50 wt. %, from 5 wt. % to 70 wt. %, from 5 wt. %, to 65 wt. %, from 5 wt. % to 60 wt. %, from 5 wt. % to 55 wt. %, from 5 wt. % to 50 wt. %, from 10 wt. % to 70 wt. %, from 10 wt. %, to 65 wt. %, from 10 wt. % to 60 wt. %, from 10 wt. % to 55 wt. %, from 10 wt. % to 50 wt. %, from 12 wt. % to 70 wt. %, from 12 wt. %, to 65 wt. %, from 12 wt. % to 60 wt. %, from 12 wt. % to 55 wt. %, from 1 wt % to 20 wt %, from 2 wt % to 15 wt %, from 3 wt % to 15 wt %, from 1 wt % to 10 wt %, from 12 wt. % to 50 wt. %, from 15 wt. % to 70 wt. %, from 15 wt. %, to 65 wt. %, from 15 wt. % to 60 wt. %, from 15 wt. % to 55 wt. %, or from 15 wt. % to 50 wt. %. In terms of upper limits, the adiponitrile process stream may comprise less than 70 wt. % low-boiling components, e.g., less than 65 wt. %, less than 60 wt. %, less than 55 wt. %, less than 50 wt. %, less than 20 wt %, less than 15 wt %, or less than 15 wt %. In terms of lower limits, the adiponitrile process stream may comprise greater than 0 wt. %, low-boiling components, e.g., greater than 1 wt %, greater than 2 wt %, greater than 3 wt %, greater than 5 wt. %, greater than 10 wt. %, greater than 12 wt. %, or greater than 15 wt. %.

The adiponitrile process stream also comprises high-boiling components. Generally, the high-boiling components are impurities having relatively high boiling points. For example, each of the high-boiling components may have a boiling point of greater than 395° C., e.g., greater than 400° C., greater than 405° C., greater than 408° C., greater than 410° C., or greater than 415° C. Examples of high-boiling components that may be present in the crude adiponitrile stream include isomeric tricyanohexane, tri(2-cyanoethyl)amine, and combinations thereof.

In one embodiment, the adiponitrile process stream comprises high-boiling components in an amount ranging from 0 wt. % to 50 wt. %, e.g., from 0 wt. % to 40 wt. %, from 0 wt. % to 35 wt. %, from 0 wt. % to 25 wt. %, from 0 wt. % to 20 wt. %, from 0.5 wt. % to 50 wt. %, from 0.5 wt. % to 40 wt. %, from 0.5 wt. % to 35 wt. %, from 0.5 wt. % to 25 wt. %, from 0.5 wt. % to 20 wt. %, from 1 wt. % to 50 wt. %, from 1 wt. % to 40 wt. %, from 1 wt. % to 35 wt. %, from 1 wt. % to 25 wt. %, from 1 wt. % to 20 wt. %, from 2 wt. % to 50 wt. %, from 2 wt. % to 40 wt. %, from 2 wt. % to 35 wt. %, from 2 wt. % to 25 wt. %, from 2 wt. % to 20 wt. %, from 3 wt. % to 50 wt. %, from 3 wt. % to 40 wt. %, from 3 wt. % to 35 wt. %, from 3 wt. % to 25 wt. %, from 3 wt. % to 20 wt. %, from 5 wt % to 15 wt %, from 5 wt. % to 50 wt. %, from 5 wt. % to 40 wt. %, from 5 wt. % to 35 wt. %, from 5 wt. % to 25 wt. %, or from 5 wt. % to 20 wt. %. In terms of upper limits, the adiponitrile process stream may comprise less than 50 wt. % high-boiling components, e.g., less than 40 wt. %, less than 35 wt. %, less than 30 wt. %, less than 25 wt. % or less than 20 wt. %. In terms of lower limits, the adiponitrile process stream may comprise greater than 0 wt. %, e.g., greater than 0.5 wt. %, greater than 1 wt. %, greater than 2 wt. %, greater than 3 wt. %, or greater than 5 wt. %.

In some embodiments, the adiponitrile process stream may also comprise solid impurities. These impurities may include various organic impurities that are solid under the temperature and pressure conditions. For example, the solid impurities may include solid cyanocarbon compounds. In one embodiment, the adiponitrile process stream comprises solid impurities in an amount ranging from 0 wt. % to 25 wt. %, e.g., from 0 wt. % to 20 wt. %, from 0 wt. % to 15 wt. %, or from 0 wt. % to 10 wt. %. In terms of upper limits, the adiponitrile process stream may comprise less than 25 wt. %, e.g., less than 20 wt. %, less than 15 wt. %, or less than 10 wt. %.

In some embodiments, the adiponitrile process stream comprises nitriles (generally, e.g., high boiling point and/or low boiling point nitriles). In one embodiment, the adiponitrile process stream comprises nitriles in an amount ranging from 0 wt. % to 90 wt. %, based on the total weight of the feed stream, e.g., from 0 wt. %, to 89 wt. %, from 0 wt. % to 88 wt. %, from 0 wt. % to 85 wt. %, from 0 wt. % to 84 wt. %, from 10 wt. % to 90 wt. %, from 10 wt. %, to 89 wt. %, from 10 wt. % to 88 wt. %, from 10 wt. % to 85 wt. %, from 10 wt. % to 84 wt. %, from 20 wt. % to 90 wt. %, from 20 wt. %, to 89 wt. %, from 20 wt. % to 88 wt. %, from 20 wt. % to 85 wt. %, from 20 wt. % to 84 wt. %, from 30 wt. % to 90 wt. %, from 30 wt. %, to 89 wt. %, from 30 wt. % to 88 wt. %, from 30 wt. % to 85 wt. %, from 30 wt. % to 84 wt. %, from 40 wt. % to 90 wt. %, from 40 wt. %, to 89 wt. %, from 40 wt. % to 88 wt. %, from 40 wt. % to 85 wt. %, from 40 wt. % to 84 wt. %, from 50 wt. % to 90 wt. %, from 50 wt. %, to 89 wt. %, from 50 wt. % to 88 wt. %, from 50 wt. % to 85 wt. %, or from 50 wt. % to 84 wt. %. In terms of upper limits, the adiponitrile process stream may comprise less than 90 wt. % nitriles, e.g., 89 wt. %., less than 88 wt. %, less than 85 wt. %, or less than 84 wt. %, In terms of lower limits, the adiponitrile process stream may comprise greater than 0 wt. % nitriles, e.g., greater than 10 wt. %, greater than 20 wt. %, greater than 30 wt. %, greater than 40 wt. %, or greater than 50.

First Separating Step

As noted above, the adiponitrile process stream is separated to form the first overhead lights stream (an overhead stream) comprising TCH and low-boiling components (lights) and (optionally lower amounts of) high-boiling components (heavies) and a first bottom heavies stream (a bottom stream) comprising high-boiling components and solid impurities. The first separating step, in some cases, removes a significant portion (if not all) of the heavies and/or the solid impurities present in the adiponitrile process stream. The inventors have found that removal of the heavies prior to further processing beneficially reduces the decomposition of the high-boiling components and thereby improves the efficiency of the total purification process. Without this initial removal of heavies, additional non-TCH components are formed, which must then be separated, creating additional operations and uncertainties. Furthermore, the inventors have also found that early removal of the heavies and the solid impurities reduces fouling of columns, which improves downstream efficiency and eliminates or reduces the need for subsequent separation operations.

In some embodiments, the first separating step includes separation in a flasher, e.g., a flash evaporator. In these embodiments, the adiponitrile process stream is evaporated and separated into the first overhead lights stream and the first bottom heavies stream. Various flashers are known to those of ordinary skill in the art, and any suitable flasher may be employed as long as the separation described herein is achieved. In some embodiments, the separation in the flasher may be caused by reducing the pressure, e.g., an adiabatic flash, without heating the feed stream. In other embodiments, the separation in the flasher may be caused by raising the temperature of the feed stream without changing the pressure. In still other embodiments, the separation in the flasher may be caused by reducing the pressure while heating the feed stream.

In some embodiments, flashing includes separating the adiponitrile process stream in a flash evaporator at reduced pressure, e.g., under a vacuum. In some embodiments, the pressure in the flash evaporator is reduced to less than 25 torr, e.g., less than 20 torr, less than 10 torr, or less than 5 torr. In some embodiments, the flash vessel of the flashing step is kept at a constant temperature. In some embodiments, the temperature of the flash vessel may be from 175° C. to 235° C., e.g., from 180° C. to 230° C., from 185° C. to 225° C., or from 190° C. to 220° C.

In some embodiments, the first separating step is achieved via a wiped film evaporator (WFE). Said another way, in some embodiments, first evaporating step comprises treating the adiponitrile process stream in a WFE. Those of skill in the art will appreciate how to utilize a WFE in accordance with the processes described herein.

In some embodiments, the first separating step is achieved via a falling film evaporator. Said another way, in some embodiments, first evaporating step comprises treating the adiponitrile process stream in a falling film evaporator. Those of skill in the art will appreciate how to utilize a falling film evaporator in accordance with the processes described herein.

The first bottoms stream comprises high-boiling components (heavies). Examples of heavies that may be present in the first bottoms stream include isomeric tricyanohexane, tri(2-cyanoethyl)amine, and combinations thereof. In one embodiment, the separation step occurs in a flasher, and the first bottoms stream comprises isomeric tricyanohexane and tri(2-cyanoethyl)amine. The first bottoms stream also may comprise solid impurities. In one embodiment, the flashing step removes all (substantially all) of the solid impurities from the adiponitrile process stream. Said another way, in this embodiment, the flash overhead stream comprises effectively 0 wt. % solid impurities. In other embodiments, the flashing step may remove less than 100% of the solid impurities, e.g., less than 99.9%, less than 99%, or less than 98%.

The first overhead lights stream may comprise less than 90 wt % adiponitrile, e.g., less than 75 wt %, less than 50 wt %, less than 40 wt %, less than 35 wt %, less than 30 wt %, less than wt 20%, less than 18 wt %, less than 15 wt %, less than 12 wt %, less than 10 wt %, less than 5 wt %, less than 4 wt %, less than 3 wt %, or less than 2 wt %. In terms of ranges, the first overhead lights stream may comprise from 0.1 wt % to 90 wt % adiponitrile, e.g., from 0.1 wt % to 75 wt %, from 0.1 wt % to 40 wt %, from 0.1 wt % to 10 wt %, from 0.1 wt % to 5 wt %, from 0.5 wt % to 5 wt %, from 0.5 wt % to 3 wt %, from 0.5 wt % to 30 wt %, from 1 wt % to 20 wt %, from 2 wt % to 20 wt %, from 5 wt % to 18 wt %, or from 5 wt % to 15 wt %. In terms of lower limits, the first overhead lights stream may comprise greater than 0.1 wt % adiponitrile, e.g., greater than 0.3 wt %, greater than 0.5 wt %, greater than 0.7 wt %, greater than 1.0 wt %, greater than 1.5 wt %, greater than 2 wt %, or greater than 5 wt %.

In some embodiments, the first overhead lights stream comprises less than 99 wt. % TCH, e.g., less than 97 wt %, less than 90 wt %, less than 80 wt %, less than 70 wt %, less than 50 wt. %, less than 35 wt. %, less than 25 wt. %, less than 20 wt. %, less than 18 wt. %, less than 15 wt. %, less than 12 wt. %, less than 10 wt. %, or less than 5 wt. %. In terms of ranges, the first overhead lights stream may comprise from 0.1 wt % to 99 wt % TCH, e.g., from 50 wt % to 99 wt %, from 75 wt % to 98 wt %, from 85 wt % 98 wt %, from 90 wt % to 97 wt %, from 0.1 wt. % to 25 wt. %, from 0.5 wt. % to 23 wt. %, from 0.5 wt. % to 20 wt. %, from 1 wt. % to 15 wt. %, from 1.5 wt. % to 12 wt. %, or from 2 wt. % to 11 wt. %. In terms of lower limits, the first overhead lights stream may comprise greater than 0.1 wt. % TCH, e.g., greater than 0.3 wt. %, greater than 0.5 wt. %, greater than 0.7 wt. %, greater than 1.0 wt. %, greater than 1.5 wt. %, greater than 2 wt. %, greater than 5 wt. %, greater than 25 wt %, greater than 50 wt %, greater than 75 wt %, greater than 85 wt %, greater than 85 wt %, or greater than 90 wt %.

In one embodiment, the first overhead lights stream comprises lights in an amount ranging from 0 wt. % to 70 wt. %, e.g., from 0.1 wt % to 30 wt %, from 0.1 wt % to 50 wt %, from 0 wt. % to 25 wt. %, from 0 wt. %, to 20 wt. %, from 0 wt. % to 15 wt. %, from 0 wt. % to 10 wt. %, from 1 wt. % to 30 wt. %, from 1 wt. % to 25 wt. %, from 1 wt. %, to 20 wt. %, from 1 wt. % to 15 wt. %, from 1 wt. % to 10 wt. %, from 2 wt. % to 30 wt. %, from 2 wt. % to 25 wt. %, from 2 wt. %, to 20 wt. %, from 2 wt. % to 15 wt. %, from 2 wt. % to 10 wt. %, from 3 wt. % to 30 wt. %, from 3 wt. % to 25 wt. %, from 3 wt. %, to 20 wt. %, from 0.1 wt. %, to 10 wt. %, from 0.1 wt. %, to 5 wt. %, from 0.3 wt. %, to 3 wt. %, from 0.5 wt. %, to 2 wt. %, from 1 wt. %, to 3 wt. %, from 3 wt. % to 15 wt. %, from 3 wt. % to 10 wt. %, from 4 wt. % to 30 wt. %, from 4 wt. % to 25 wt. %, from 4 wt. %, to 20 wt. %, from 4 wt. % to 15 wt. %, from 4 wt. % to 10 wt. %, from 5 wt. % to 30 wt. %, from 5 wt. % to 25 wt. %, from 5 wt. %, to 20 wt. %, from 5 wt. % to 15 wt. %, or from 5 wt. % to 10 wt. %. In terms of upper limits, the first overhead lights stream may comprise less than 70 wt. % lights, e.g., less than 50 wt %, less than 30 wt %, less than 25 wt. %, less than 20 wt. %, less than 15 wt. %, less than 10 wt. %, less than 5 wt %, less than 3 wt %, or less than 2 wt %. In terms of lower limits, the first overhead lights stream may comprise greater than 0 wt. % lights, e.g., greater than 0.1 wt %, greater than 0.3 wt %, greater than 0.5 wt %, greater than 1 wt. %, greater than 2 wt. %, greater than 3 wt. %, greater than 4 wt. %, or greater than 5 wt. %.

In one embodiment, the first overhead lights stream comprises heavies in an amount ranging from 0 wt. % to 20 wt. %, e.g., from 0 wt. % to 15 wt. %, from 0 wt. % to 10 wt. %, from 0 wt. % to 8 wt. %, from 0 wt. % to 5 wt. %, from 0.5 wt. % to 20 wt. %, from 0.5 wt. % to 15 wt. %, from 0.5 wt. % to 10 wt. %, from 0.5 wt. % to 8 wt. %, from 0.5 wt. % to 5 wt. %, from 1 wt. % to 20 wt. %, from 1 wt. % to 15 wt. %, from 1 wt. % to 10 wt. %, from 1 wt. % to 8 wt. %, from 1 wt. % to 5 wt. %, from 1.5 wt. % to 20 wt. %, from 1.5 wt. % to 15 wt. %, from 1.5 wt. % to 10 wt. %, from 1.5 wt. % to 8 wt. %, from 1.5 wt. % to 5 wt. %, from 2 wt. % to 20 wt. %, from 2 wt. % to 15 wt. %, from 2 wt. % to 10 wt. %, from 2 wt. % to 8 wt. %, from 2 wt. % to 5 wt. %, from 2.5 wt. % to 20 wt. %, from 2.5 wt. % to 15 wt. %, from 2.5 wt. % to 10 wt. %, from 2.5 wt. % to 8 wt. %, or from 2.5 wt. % to 5 wt. %. In terms of upper limits, the first overhead lights stream may comprise less than 20 wt. % heavies, e.g., less than 15 wt. %, less than 10 wt. %, less than 8 wt. %, or less than 5 wt. %. In terms of lower limits, the first overhead lights stream may comprise greater than 0 wt. % heavies, e.g., greater than 0.5 wt. %, greater than 1 wt. %, greater than 1.5 wt. %, greater than 2 wt. %, or greater than 2.5 wt. %.

In some cases, the first separating step removes a significant portion of the heavies from the first overhead lights stream. Said another, the first overhead lights stream comprises low amounts, if any, of the heavies initially present in the adiponitrile stream. In some embodiments, the first intermediate adiponitrile stream comprises less than 70% of the heavies present in the feed stream, e.g., less than 65%, less than 60%, less than 55%, or less than 50%.

In one embodiment, the first overhead lights stream comprises heavies in an amount ranging from 0 wt. % to 20 wt. %, e.g., from 0 wt. % to 15 wt. %, from 0 wt. % to 10 wt. %, from 0 wt. % to 8 wt. %, from 0 wt. % to 5 wt. %, from 0.5 wt. % to 20 wt. %, from 0.5 wt. % to 15 wt. %, from 0.5 wt. % to 10 wt. %, from 0.5 wt. % to 8 wt. %, from 0.5 wt. % to 5 wt. %, from 1 wt. % to 20 wt. %, from 1 wt. % to 15 wt. %, from 1 wt. % to 10 wt. %, from 1 wt. % to 8 wt. %, from 1 wt. % to 5 wt. %, from 1.5 wt. % to 20 wt. %, from 1.5 wt. % to 15 wt. %, from 1.5 wt. % to 10 wt. %, from 1.5 wt. % to 8 wt. %, from 1.5 wt. % to 5 wt. %, from 2 wt. % to 20 wt. %, from 2 wt. % to 15 wt. %, from 2 wt. % to 10 wt. %, from 2 wt. % to 8 wt. %, from 2 wt. % to 5 wt. %, from 2.5 wt. % to 20 wt. %, from 2.5 wt. % to 15 wt. %, from 2.5 wt. % to 10 wt. %, from 2.5 wt. % to 8 wt. %, or from 2.5 wt. % to 5 wt. %. In terms of upper limits, the first overhead lights stream may comprise less than 20 wt. % heavies, e.g., less than 15 wt. %, less than 10 wt. %, less than 8 wt. %, or less than 5 wt. %. In terms of lower limits, the first intermediate overhead lights may comprise greater than 0 wt. % heavies, e.g., greater than 0.5 wt. %, greater than 1 wt. %, greater than 1.5 wt. %, greater than 2 wt. %, or greater than 2.5 wt. %.

Second Separating Step

As noted above, the first overhead lights stream is separated in a second separating step to form the second overhead lights stream comprising low-boiling components (lights), a second bottom heavies stream comprising high-boiling components (heavies), and a TCH stream. The separating step, in some cases, removes a significant portion (if not all) of the low-boiling components and high-boiling components present in the first overhead lights stream. In some embodiments, the separating step comprise two columns and the first distillation column forms a lights stream as an overhead stream (comprising adiponitrile) and a second bottoms stream. The second bottoms stream is then separated in a second distillation column to form the heavies stream as a third bottoms stream and the TCH stream as a third overhead stream.

The second separating step may include separation of the first overheard stream in one or more distillation columns and/or in one or more flash evaporators. The structure of the one or more distillation columns may vary widely. Various distillation columns are known to those of ordinary skill in the art, and any suitable column may be employed in the second separation step as long as the separation described herein is achieved. For example, the distillation column may comprise any suitable separation device or combination of separation devices. For example, the distillation column may comprise a column, e.g., a standard distillation column, an extractive distillation column and/or an azeotropic distillation column. Similarly, as noted above, various flashers are known to those of ordinary skill in the art, and any suitable flasher may be employed in the second separation stepas long as the separation described herein is achieved. For example, the flasher may comprise an adiabatic flash evapaorator, a heated flash evaporator, or a wipe film evaporator, or combinations thereof.

Embodiments of the second separating step may include any combination of one or more distillation columns and/or one or more flashers, as long as the aforementioned streams are formed.

In some cases, the separating step comprises one or more columns, e.g., two columns. In some embodiments, the separating step comprise two columns and the first distillation column forms a lights stream as an overhead stream and an intermediate bottoms stream. The intermediate bottoms stream is then separated in a second distillation column to form the heavies stream as a bottoms stream and the TCH stream as an overhead stream.

As noted above, low pressure column operation has been found to be unexpectedly effective. For example, low pressure operation surprisingly provides for improved efficiency of the separation, e.g., by reducing or eliminating decomposition and/or mitigates any detrimental factors that may arise with high temperature reboiler operations, e.g., decomposition. In some embodiments, at least one of the distillation columns of the second separating is a low pressure distillation column. In one embodiment, the low pressure distillation column(s) is operated with a column top pressure less than 100 mm Hg, e.g., less than 80 mm Hg, less than 60 mm Hg, less than 40 mm Hg, less than 20 mm Hg, less than 15 mm Hg, less than 10 mmHg, less than 5 mm Hg, or less than 3 mm Hg. In one embodiment, the low pressure distillation column(s) is operated with a column bottom pressure less than 100 mm Hg, e.g., less than 80 mm Hg, less than 60 mm Hg, less than 40 mm Hg, less than 20 mm Hg, less than 15 mm Hg, less than 10 mmHg, less than 5 mm Hg, or less than 3 mm Hg.

In some aspects, the purification processes may employ high temperature reboilers. In some cases, the high temperature reboiler and the low pressure column synergistically achieve a highly effective separation. A reboiler is a heat exchanger used to provide heat to the distillation column and thereby boil liquid in the bottom of the distillation column. In some embodiments of the process, reboilers of one or more (e.g., all) distillation columns in the second separating step operate at high temperatures. In one embodiment, the reboiler operates at a temperature greater than 235° C., e.g., greater than 240° C., greater than 250° C., greater than 275° C., greater than 300° C., greater than 325° C., greater than 350° C., or greater than 375° C. The aforementioned operating parameters are applicable to other columns as well.

In one embodiment, for example, the second separating step comprises separating the first overhead lights stream in two consecutive distillation columns. In this embodiment, the first overhead lights stream is separated in a first distillation column. A second overhead lights stream is collected from the overhead (e.g., the column top and/or a relatively high side draw) of the first distillation column, and a second bottom (intermediate) heavies stream is collected from the bottom (e.g., the column bottom and/or a relatively low side draw) of the first distillation column. At least a portion of the second bottom (intermediate) heavies stream is then separated in a second distillation column. A third bottom heavies stream is collected from the bottom (e.g., the column bottom and/or a relatively low side draw) of the second distillation column. The TCH stream is collected from the overhead (e.g., column top and/or a relatively high side draw) of the second distillation column, e.g., as a third overhead lights stream.

In another embodiment, the second separating step comprises separating the first overhead lights stream in a distillation column and an evaporator (e.g., flasher, WFE, or falling film evaporator). In this embodiment, the first distillation columns is separated in a first distillation column. A second overhead lights stream is collected from the overhead (e.g., the column top and/or a relatively high side draw) of the first distillation column, a second bottom heavies stream is collected from the bottom (e.g., the column bottom and/or a relatively low side draw) of the first distillation column, and a side draw is collected is a side cut of the first distillation column. At least a portion of the side draw is then separated draw in an evaporator. A third overhead lights stream is collected from the top of the evaporator, and the TCH stream is collected from the bottom of the evaporator, e.g., as a third bottom heavies stream.

In another embodiment, the second separating step comprises separating the first overhead lights stream in a three distillation columns. In this embodiment, the first overhead lights stream is separated in a first distillation column. A second overhead lights stream is collected from the overhead (e.g., the column top and/or a relatively high side draw) of the first distillation column, and a second bottom heavies stream is collected from the bottom (e.g., the column bottom and/or a relatively low side draw) of the first distillation column. At least a portion of the second bottom heavies stream is then separated in a second distillation column. A third overhead lights stream is collected from the overhead (e.g., the column top and/or a relatively high side draw) of the second distillation column, and third bottom heavies stream is collected from the bottom (e.g., the column bottom and/or a relatively low side draw) of the second distillation column. At least a portion of the third overhead lights stream is then separated in a third distillation column. A fourth bottom heavies stream is collected from the bottom (e.g., the column bottom and/or a relatively low side draw) of the third distillation column, and the TCH stream is collected from the top (e.g., the column top and/or a relatively high side draw) of the third distillation column, e.g., as a fourth overhead lights stream.

In another embodiment, the second separating step comprises separating the first overhead lights stream in a two distillation columns and an evaporator (e.g., flasher, WFE, or falling film evaporator). In this embodiment, the first overhead lights stream is separated in a first distillation column. A second overhead lights stream is collected from the overhead (e.g., the column top and/or a relatively high side draw) of the first distillation column, and a second bottom heavies stream is collected from the bottom (e.g., the column bottom and/or a relatively low side draw) of the first distillation column. At least a portion of the second bottom heavies stream is then separated in a second distillation column. A third overhead lights stream is collected from the overhead (e.g., the column top and/or a relatively high side draw) of the second distillation column, and third bottom heavies stream is collected from the bottom (e.g., the column bottom and/or a relatively low side draw) of the second distillation column. At least a portion of the third overhead lights stream is then separated in an evaporator. A fourth overhead lights stream is collected from the top of the evaporator, and the TCH stream is collected from the bottom of the evaporator, e.g., as a fourth bottom heavies stream.

Second Overhead Lights Stream

In some embodiments, the second overhead lights stream may comprise greater than 1 wt % adiponitrile, e.g., greater than 5 wt %, greater than 6 wt %, greater than 10 wt %, greater than 20 wt %, greater than 25 wt %, greater than 30 wt %, greater than 35 wt %, or greater than 50 wt %. In terms of ranges, the second overhead lights stream may comprise from 1 wt % to 95 wt % adiponitrile, from 5 wt % to 95 wt %, from 7 wt % to 75 wt %, from 5 wt % to 35 wt %, from 6 wt % to 30 wt %, from 25 wt % to 75 wt %, from 30 wt % to 70 wt %, or from 40 wt % to 60 wt %. In terms of lower limits, the second overhead lights stream comprises less than 95 wt % TCH, e.g., less than wt 90%, less than 85 wt %, less than 80 wt %, less than 75 wt %, less than 65 wt %, or less than 60 wt %.

In some embodiments, the second overhead lights stream may comprise greater than 1 wt % TCH, e.g., greater than 5 wt %, greater than 10 wt %, greater than 20 wt %, greater than 25 wt %, greater than 30 wt %, greater than 35 wt %, greater than 50 wt %, greater than 60 wt %, or greater than 70 wt %. In terms of ranges, the second overhead lights stream may comprise from 1 wt % to 95 wt % TCH, from 5 wt % to 95 wt %, from 20 wt % to 95 wt %, from 30 wt % to 95 wt %, from 45 wt % to 80 wt %, from 50 wt % to 95 wt %, from 60 wt % to 90 wt %, from 70 wt % to 90 wt %, from 25 wt % to 75 wt %, from 30 wt % to 70 wt %, or from 40 wt % to 60 wt %. In terms of lower limits, the second overhead lights stream comprises less than 95 wt % TCH, e.g., less than wt 90%, less than 85 wt %, less than 80 wt %, less than 75 wt %, less than 65 wt %, or less than 60 wt %.

The second overhead lights stream may comprise less than 70 wt % lights, e.g., less than 50 wt %, less than 35 wt %, less than 25 wt %, less than 20 wt %, less than 15 wt %, less than 12 wt %, or less than 10 wt %. In terms of ranges, the second overhead lights stream may comprise from 0.1 wt % to 70 wt % lights, e.g., from 0.1 wt % to 50 wt %, from 0.1 wt % to 25 wt %, from 0.5 wt % to 25 wt %, from 10 wt % to 25 wt %, from 1 wt % to 20 wt %, from 2 wt % to 18 wt %, from 2 wt % to 15 wt %, or from 2 wt % to 10 wt %. In terms of lower limits, the second overhead lights stream may comprise greater than 0.1 wt % lights, e.g., greater than 0.3 wt %, greater than 0.5 wt %, greater than 0.7 wt %, greater than 1.0 wt %, greater than 1.5 wt %, greater than 2 wt %, or greater than 5 wt %. As noted above, in some cases, the term "lights" refers to components that have lower boiling points, e.g., lower boiling points than adiponitrile or lower boiling points than TCH.

The second overhead lights stream may comprise high-boiling components (heavies). In one embodiment, the second overhead lights stream comprises high-boiling components in an amount ranging from 0.1 wt % to 50 wt %, e.g., from 0.1 wt % to 20 wt %, from 0.1 wt % to 10 wt %, from 0.5 wt % to 10 wt %, from 0.5 wt % to 5 wt %, from 1 wt % to 3 wt %, from 5 wt % to 50 wt %, e.g., from 5 wt % to 45 wt %, from 5 wt % to 40 wt %, from 5 wt % to 35 wt %, from 5 wt % to 30 wt %, from 8 wt % to 50 wt %, from 8 wt % to 45 wt %, from 8 wt % to 40 wt %, from 8 wt % to 35 wt %, from 8 wt % to 30 wt %, from 10 wt % to 50 wt %, from 10 wt % to 45 wt %, from 10 wt % to 40 wt %, from 10 wt % to 35 wt %, from 10 wt % to 30 wt %, from 12 wt % to 50 wt %, from 12 wt % to 45 wt %, from 12 wt % to 40 wt %, from 12 wt % to 35 wt %, from 12 wt % to 30 wt %, from 15 wt % to 50 wt %, from 15 wt % to 45 wt %, from 15 wt % to 40 wt %, from 15 wt % to 35 wt %, or from 15 wt % to 30 wt %. In terms of upper limits, the second overhead lights stream may comprise less than 50 wt % high-boiling components, e.g., less than 45 wt %, less than 40 wt %, less than 35 wt %, less than 30 wt %, less than 20 wt %, less than 10 wt %, less than 5 wt %, or less than 3 wt %. In terms of lower limits, the (second) intermediate adiponitrile stream may comprise greater than 0.1 wt % high-boiling components, e.g., greater than 0.5 wt %, greater than 1 wt %, greater than 5 wt %, greater than 8 wt %, greater than 10 wt %, greater than 12 wt %, or greater than 15 wt %.

In some cases, the separation of the second overhead lights stream may be achieved in a two column system. The first column yields the second overhead lights stream and an intermediate bottoms stream, which is fed to the second column. The intermediate bottoms stream may comprise high amounts of TCH and may then be further separated, e.g., in one or more additional columns. The intermediate bottoms stream may comprise high amounts of TCH and may then be further separated, e.g., in one or more additional columns. For example, the intermediate bottoms stream, in some embodiments, comprises TCH in higher amounts ranging from 90 wt % to 100 wt %, e.g., from 90 wt % to 99.9 wt %, from 90 wt % to 99 wt %, from 90 wt % to 98 wt %, from 92.5 wt % to 100 wt %, from 92.5 wt % to 99.9 wt %, from 92.5 wt % to 99 wt %, from 92.5 to 98 wt %, from 95 wt % to 100 wt %, from 95 wt % to 99.9 wt %, from 95 wt % to 99 wt %, from 95 to 98 wt %, from 97.5 wt % to 100 wt %, from 97.5 wt % to 99.9 wt %, from 97.5 to 99 wt %, or from 97.5 to 98 wt %. In terms of upper limits, the intermediate bottoms stream may comprise less than 100 wt % TCH, e.g., less than 99.9 wt %, less than 99 wt %, or less than 98 wt %. In terms of lower limits, the intermediate bottoms stream may comprise greater than 90 wt %, e.g., greater than 92.5 wt %, greater than 95 wt %, or greater than 97.5 wt %.

The intermediate bottoms stream may further comprise small amounts of adiponitrile and lights (amounts similar to those discussed herein for the TCH stream). The intermediate bottoms stream may further comprise heavies (amounts similar to those discussed herein for the (second) overhead lights stream.

In some case, the intermediate bottoms stream may be further separated, e.g., to yield a bottoms heavies stream and the TCH stream.

(Second Bottoms) Heavies Stream

The second bottom heavies stream comprises high-boiling components (heavies). In one embodiment, the second bottom heavies stream comprises high-boiling components in an amount ranging from 0.1 wt % to 50 wt %, e.g., from 0.1 wt % to 20 wt %, from 0.1 wt % to 10 wt %, from 0.5 wt % to 10 wt %, from 0.5 wt % to 5 wt %, from 1 wt % to 3 wt %, from 5 wt % to 50 wt %, e.g., from 5 wt % to 45 wt %, from 5 wt % to 40 wt %, from 5 wt % to 35 wt. %, from 5 wt. % to 30 wt. %, from 8 wt. % to 50 wt. %, from 8 wt. % to 45 wt. %, from 8 wt. % to 40 wt. %, from 8 wt. % to 35 wt. %, from 8 wt. % to 30 wt. %, from 10 wt. % to 50 wt. %, from 10 wt. % to 45 wt. %, from 10 wt. % to 40 wt. %, from 10 wt. % to 35 wt. %, from 10 wt. % to 30 wt. %, from 12 wt. % to 50 wt. %, from 12 wt. % to 45 wt. %, from 12 wt. % to 40 wt. %, from 12 wt. % to 35 wt. %, from 12 wt. % to 30 wt. %, from 15 wt. % to 50 wt. %, from 15 wt. % to 45 wt. %, from 15 wt. % to 40 wt. %, from 15 wt. % to 35 wt. %, or from 15 wt. % to 30 wt. %. In terms of upper limits, the second bottom heavies stream may comprise less than 50 wt. % high-boiling components, e.g., less than 45 wt. %, less than 40 wt. %, less than 35 wt. %, less than 30 wt. %, less than 20 wt. %, less than 10 wt. %, less than 5 wt. %, or less than 3 wt. %. In terms of lower limits, the second bottom heavies stream may comprise greater than 0.1 wt. % high-boiling components, e.g., greater than 0.5 wt %, greater than 1 wt. %, greater than 5 wt. %, greater than 8 wt. %, greater than 10 wt. %, greater than 12 wt. %, or greater than 15 wt. %.

In some embodiments, the heavies stream, which may, in some cases be a bottoms stream from a second column of a two column system, may comprise high amounts of TCH as well as heavies. In some cases, the heavies stream may comprise TCH in amounts ranging from 90 wt. % to 100 wt. %, e.g., from 90 wt. % to 99.9 wt. %, from 90 wt. % to 99 wt. %, from 90 wt. % to 98 wt. %, from 92.5 wt. % to 100 wt. %, from 92.5 wt. % to 99.9 wt. %, from 92.5 wt. % to 99 wt. %, from 92.5 to 98 wt. %, from 95 wt. % to 100 wt. %, from 95 wt. % to 99.9 wt. %, from 95 wt. % to 99 wt. %, from 95 to 98 wt. %, from 97.5 wt. % to 100 wt. %, from 97.5 wt. % to 99.9 wt. %, from 97.5 wt. % to 99 wt. %, or from 97.5 to 98 wt. %. In terms of upper limits, the heavies stream may comprise less than 100 wt. % TCH, e.g., less than 99.9 wt. % less than 99 wt. %, or less than 98 wt. %. In terms of lower limits, the heavies stream may comprise greater than 90 wt. %, e.g., greater than 92.5 wt. %, greater than 95 wt. %, or greater than 97.5 wt. %.

In some embodiments, the heavies stream may comprise low amounts of lights and/or adiponitrile (amounts similar to those discussed herein for the TCH stream).

TCH Stream

The TCH stream may comprise greater than 1 wt % TCH, e.g., greater than 5 wt %, greater than 10 wt %, greater than 20 wt %, greater than 25 wt %, greater than 30 wt %, greater than 35 wt %, greater than 50 wt %, greater than 75 wt %, greater than 85 wt %, greater than 90 wt %, greater than 93%, or greater than 95 wt %. In terms of ranges, the TCH stream may comprise from 1 wt % to 99.9 wt % TCH, e.g., from 25 wt % to 99.9 wt %, from 50 wt % to 99.9 wt %, from 75 wt % to 99.9 wt %, from 90 wt % to 99.9 wt %, from 85 wt % to 99.5 wt %, from 5 wt % to 99 wt %, from 50 wt % to 99 wt %, from 5 wt % to 95 wt %, from 25 wt % to 90 wt %, from 45 wt % to 90 wt %, or from 50 wt % to 85 wt %. In terms of upper limits, the TCH stream comprises less than 99.9 wt % TCH, e.g., less than 99 wt %, less than 99.5 wt %, less than 95 wt %, less than wt 90%, less than 85 wt %, less than 80 wt %, less than 75 wt %, or less than 65 wt %.

In some embodiments, the TCH stream comprises TCH in higher amounts ranging from 90 wt. % to 100 wt. %, e.g., from 90 wt. % to 99.9 wt. %, from 90 wt. % to 99 wt. %, from 90 wt. % to 98 wt. %, from 92.5 wt. % to 100 wt. %, from 92.5 wt. % to 99.9 wt. %, from 92.5 wt. % to 99 wt. %, from 92.5 to 98 wt. %, from 95 wt. % to 100 wt. %, from 95 wt. % to 99.9 wt. %, from 95 wt. % to 99 wt. %, from 95 to 98 wt. %, from 97.5 wt. % to 100 wt. %, from 97.5 wt. % to 99.9 wt. %, from 97.5 to 99 wt. %, or from 97.5 to 98 wt. %. In terms of upper limits, the TCH stream may comprise less than 100 wt. % TCH, e.g., less than 99.9 wt. % less than 99 wt. %, or less than 98 wt. %. In terms of lower limits, the TCH stream may comprise greater than 90 wt. %, e.g., greater than 92.5 wt. %, greater than 95 wt. %, or greater than 97.5 wt. %. Conventional processes have been unable to achieve such high TCH purity levels.

In one embodiment, the TCH stream comprises impurities, e.g., heavies and/or lights, in an amount ranging from 0 wt. % to 10 wt. %, e.g., from 0 wt. % to 7.5 wt. %, from 0 wt. % to 5 wt. %, from 0 wt. % to 2.5 wt. %, from 0.1 wt. % to 10 wt. %, from 0.1 wt. % to 7.5 wt. %, from 0.1 wt. % to 5 wt. %, from 0.1 wt. % to 2.5 wt. %, 0.1 wt. % to 1.5 wt. %, 0.2 wt. % to 1.2 wt. %, 0.3 wt. % to 1.5 wt. %, 0.5 wt. % to 1.0 wt. %, from 1 wt. % to 10 wt. %, from 1 wt. % to 7.5 wt. %, from 1 wt. % to 5 wt. %, from 1 wt. % to 2.5 wt. %, from 2 wt. % to 10 wt. %, from 2 wt. % to 7.5 wt. %, from 2 wt. % to 5 wt. %, or from 2 wt. % to 2.5 wt. %. In terms of upper limits, the TCH stream may comprise less than 10 wt. % impurities, e.g., less than 7.5 wt. %, less than 5 wt. %, less than 2.5 wt. %, less than 1.5 wt. %, less than 1.2 wt. %, or less than 1.0 wt. %. In terms of lower limits, the TCH stream may comprise greater than 0 wt. % impurities, e.g., greater than 0.1 wt. %, greater than 1 wt. %, or greater than 2 wt. %. The TCH stream may comprise amines and/or nitriles in these amounts. In some cases, the use of lower pressures in the separation surprisingly provides for improved separation of components having boiling points close to that of TCH, e.g., CVA. These ranges and limits apply to heavies and lights individually or combined.

In one embodiment, the TCH stream comprises from 0 wt. % to 0.05 wt. % adiponitrile, from 0 wt. % to 0.1 wt. % di(2-cyanoethyl) amine, from 0 wt. % to 0.05 wt. % cyanovaleramide, and from 0 wt. % to 0.05 wt. % tri(2-cyanoethyl) amine.

The TCH stream may comprise less than 25 wt. % adiponitrile, e.g., less than 23 wt. %, less than 20 wt. %, less than 18 wt. %, less than 15 wt. %, less than 12 wt. %, less than 10 wt. %, less than 8 wt. %, less than 5 wt. %, less than 3 wt. %, less than 1 wt. %, less than 0.05 wt. %, or less than 0.03 wt. %. In terms of ranges, the TCH stream may comprise from 0.001 wt. % to 25 wt. % adiponitrile, e.g., from 0.05 wt. % to 5 wt. %, from 0.1 wt. % to 25 wt. %, from 0.5 wt. % to 22 wt. %, from 1 wt. % to 20 wt. %, from 2 wt. % to 20 wt. %, or from 5 wt. % to 18 wt. %. In terms of lower limits, the TCH stream may comprise greater than 0.001 wt. % adiponitrile, e.g., greater than 0.01 wt %, greater than 0.01 wt. %, greater than 0.5 wt. %, greater than 1.0 wt. %, greater than 2.0 wt. %, greater than 5.0 wt. %, greater than 10 wt. %, or greater than 15 wt. %.

Purification

In some cases, the first overhead stream (from a first column) is purified, optionally via one or more distillation columns, to form a purified adiponitrile stream comprising at greater than 50 wt % adiponitrile. In some cases, the first overhead stream may be purified using existing purification equipment outside of the process, e.g., in a separation train for a different process.

In some embodiments, the purified adiponitrile stream comprises greater than 10 wt % adiponitrile, e.g., greater than 25 wt %, greater than 50 wt %, greater than 75 wt %, greater than 90 wt %, greater than 92 wt %, greater than 95 wt %, or greater than 97 wt %. In terms of ranges, the purified adiponitrile stream may comprise from 50 wt % to 100 wt % adiponitrile, e.g., from 50 wt % to 99.5 wt %, from 65 wt % to 99 wt %, from 75 wt % to 99 wt %, from 90 wt % to 97 wt %, or from 90 wt % to 95 wt %.

In some cases, both the purified adiponitrile stream and the TCH stream exist (as described herein). In some embodiments, the purified adiponitrile stream comprises greater than 95 wt % adiponitrile and the TCH stream comprises greater than 95 wt % TCH.

In some cases, the purification of the first overhead stream may be conducted in an outside system, e.g., a refinement process, for example in an adiponitrile production process.

Decomposition

As noted above, the inventors now have found that, in conventional adiponitrile purification processes, certain high-boiling components are prone to decomposition into impurities having both higher boiling points and/or lower boiling points. The inventors have also found that even adiponitrile and TCH can decompose when exposed to high pressures temperatures in conventional processes. In particular, the inventors have now found that prolonged exposure to high pressures temperatures, such as in columns, contributes to the decomposition of high-boiling components. Furthermore, the inventors have found that as temperatures increase, rates of decomposition increase.

Conventional processes typically require the exposing process streams to high temperatures due to the presence of high-boiling components. TCH, for example, of about 407° C. at atmospheric pressure. As can be appreciated by those skilled in the art, purification of TCH therefore conventionally requires exposing process streams to high temperatures, e.g., at least 350° C., at least 375° C., at least 400° C., or at least 410° C. At these high temperatures, however, the present inventors have found that high-boiling components, such as TCH and adiponitrile, rapidly decompose. As a result, conventional processes experience high inefficiencies. By utilizing the specific process parameters disclosed herein, however, this decomposition can be effectively mitigated or eliminated.

In one aspect, the purification process may inhibit decomposition by reducing the residence time during which process streams are exposed to high temperatures, e.g., in a separation operation. Generally, process streams may be exposed to high temperatures and/or pressures in a column. In order to reduce prolonged exposure, the process may reduce the residence time of a stream in a given column (or flasher). For example, the process may control the residence time of the (first or second) intermediate adiponitrile stream or the TCH stream (or another purification stream) in a column. In one embodiment, the process limits the residence time of the (first or second) intermediate adiponitrile stream or the TCH stream (or another purification stream) in a column to less than 8 hours, e.g., less than 7 hours, less than 6 hours, less than 5 hours, or less than 4 hours.

In some aspects, the purification processes may inhibit decomposition by operating one or more (e.g., all) distillation columns in the second separating step at reduced pressure. At lower pressures, the boiling points of the high-boiling components are reduced, allowing for effective separation of the process streams with exposure to high temperatures. Said another way, at least one of the distillation columns of the second separating is a low pressure distillation column. In one embodiment, the low pressure distillation column(s) is operated with a column top pressure less than 100 mm Hg, e.g., less than 80 mm Hg, less than 60 mm Hg, less than 40 mm Hg, less than 20 mm Hg, less than 15 mm Hg, less than 10 mmHg, less than 5 mm Hg, or less than 3 mm Hg. In one embodiment, the low pressure distillation column(s) is operated with a column bottom pressure less than 100 mm Hg, e.g., less than 80 mm Hg, less than 60 mm Hg, less than 40 mm Hg, less than 20 mm Hg, less than 15 mm Hg, less than 10 mmHg, less than 5 mm Hg, or less than 3 mm Hg. In one embodiment, the low pressure distillation column(s) is operated under vacuum.

In one aspect, the separation and/or purification steps may inhibit decomposition by reducing the exposure of process streams to high temperatures. For example, the process may control the temperature to which the (first or second) intermediate adiponitrile stream of the TCH stream (or another purification stream) is exposed, e.g., in a separation step. In one embodiment, the purification process limits the temperature at which separation step(s) are conducted. For example, operation temperature may be limited to less than 350° C., e.g., less than 325° C., less than 300° C., less than 275° C., or less than 250° C., In terms of ranges operation temperature may range from 225° C. to 350° C., e.g., from 250° C. to 325° C. or from 275° C. to 300° C., or from 250° C. to 275° C.

In some aspects, the process may control both the temperature to which a stream is exposed and the time for which it is exposed to that temperature. For example, the process may control the residence time of the (first or second) intermediate adiponitrile stream or the TCH stream (or another purification stream) in a column as well as the temperature of that distillation column. In one embodiment, the residence time of a stream in temperatures above 230° C. is less than 8 hours. The aforementioned ranges and limits for temperature and residence time may be combined with one another.

In some aspects, the process may control both the temperature to which a stream is exposed and the pressure to which it is exposed. In one embodiment, the process may be controlled such that the stream is not exposed to temperatures above 300° C. or pressures above 35 torr.

In other aspects, the process may inhibit decomposition by utilizing columns with certain physical features. In particular, the distillation columns employed in the purification process may have certain shapes. In some embodiments, the distillation columns have relatively small sumps to minimize exposure to high temperatures. In these embodiments, the sumps of each column may taper to a smaller diameter, which allows or reduced exposure to higher temperatures.

To effectively operate at such high temperatures, the reboiler may require special systems. In some embodiments, the reboiler utilizes a hot oil system sufficient to support high temperatures. Those of skill in the art will appreciate how to utilize a hot oil system in accordance with the processes described herein.

These modifications to conventional purification processes reduce the decomposition of high-boiling components. In some embodiments, these modifications increase the efficiency of separation. Operating distillation columns at low pressure (e.g., under vacuum), for example, reduces the boiling points of the components to be separated. This allows the streams to separate without exposing high-boiling components to high temperatures at which they may decompose. in the first overhead stream that decompose during the second separating step.

Similarly, operating distillation columns with high temperature reboilers (e.g., reboilers utilizing a hot oil system) has been found to improve the efficiency. Although exposure to high temperatures contributes to decomposition, the present inventors have surprisingly found that high temperature reboilers can actually reduce decomposition. Without being bound by theory, it is believed that this is due to increased rate of evaporation and thereby increased rate of separation of the components within the column. As a result, the retention time of a given stream in the column can be reduced.

In one embodiment, the amount of high-boiling components in the first overhead lights stream, the second bottom heavies stream, or the TCH stream (or another process stream) that decompose is less than 50 wt. % of the high-boiling components in the stream, e.g., less than 45 wt. %, less than 40 wt. %, or less than 30 wt. %. In terms of lower limits, the amount of high-boiling components that decompose may be greater than 0 wt. % of the high-boiling components in the stream, e.g., greater than 5 wt. %, greater than 10 wt. %, or greater than 15 wt. %. In terms of ranges, the amount of high-boiling components that decompose may be from 0 wt. %. to 50 wt. %, e.g., from 0 wt. % to 45 wt. %, from 0 wt. % to 40 wt. %, from 0 wt. % to 30 wt. %, from 5 wt. % to 50 wt. %, from 5 wt. % to 45 wt. %, from 5 wt. % to 40 wt. %, from 5 wt. % to 30 wt. %, from 10 wt. % to 50 wt. %, from 10 wt. % to 45 wt. %, from 10 wt. % to 40 wt. %, from 10 wt. % to 30 wt. %, from 15 wt. % to 50 wt. %, from 15 wt. % to 45 wt. %, from 15 wt. % to 40 wt. %, or from 15 wt. % to 30 wt. %.

In some embodiments, the various process streams individually comprise less than 1 wt. % decomposition products of high-boiling components, e.g., less than 0.8 wt. %, less than 0.5 wt. %, less than 0.3 wt. %, less than 0.1 wt. %, less than 0.05 wt. %, or less than 0.01 wt. %.

As noted above, the high-boiling components may decompose into other high-boiling impurities and/or into low-boiling impurities. In some cases, the high-boiling components may decompose into other high-boiling impurities that were not otherwise present in the system. Said another way, the decomposition may cause the total number of high-boiling impurity compounds in the system to increase. By inhibiting decomposition, as described herein, the increase in the total number of high-boiling impurity compounds present in the system, caused by decomposition, may be reduced.

Recycle Step

In some embodiments, the process comprises a recycle step of recycling at least a portion of a (bottoms or heavies) stream formed during the separation steps to a point upstream (target). For example, the recycling step may comprise recycling at least a portion of the heavies stream of one of the columns or flashers to a point upstream in the process. In some embodiments, the recycling step comprises recycling at least a portion of the heavies stream of the separation step to the flasher overhead stream of the flashing step. In some embodiments, the recycling step comprises recycling at least a portion of the a bottoms stream of the purification step to the flasher overhead stream of the flashing step and/or the bottoms stream of the separation step.

In one embodiment, the recycled stream comprises heavies, and the concentration of these heavies surprisingly affects the purity of the resultant TCH stream and may help to control the concentration of high-boiling components in the overhead streams to be from 0 wt. % to 10 wt. %. In some cases, the concentration of high-boiling components in the recycle streams leads to lesser amounts of high-boiling components in the various overhead streams, which in turn leads to higher purity of adiponitrile and/or TCH.

In some cases, the recycled stream comprises heavies in an amount ranging from 0 wt. % to 40 wt. %, e.g., from 0 wt. % to 37.5 wt. %, from 0 wt. % to 35 wt. %, from 0 wt. % to 32.5 wt. %, from 0 wt. % to 30 wt. %, from 5 wt. % to 40 wt. %, from 5 wt. % to 37.5 wt. %, from 5 wt. % to 35 wt. %, from 5 wt. % to 32.5 wt. %, from 5 wt. % to 30 wt. %, from 10 wt. % to 40 wt. %, from 10 wt. % to 37.5 wt. %, from 10 wt. % to 35 wt. %, from 10 wt. % to 32.5 wt. %, from 10 wt. % to 30 wt. %, from 15 wt. % to 40 wt. %, from 15 wt. % to 37.5 wt. %, from 15 wt. % to 35 wt. %, from 15 wt. % to 32.5 wt. %, from 15 wt. % to 30 wt. %, from 20 wt. % to 40 wt. %, from 20 wt. % to 37.5 wt. %, from 20 wt. % to 35 wt. %, from 20 wt. % to 32.5 wt. %, or from 20 wt. % to 30 wt. %. In terms of upper limits, the recycled stream may comprise less than 40 wt. % high-boiling components, e.g., less than 37.5 wt. %, less than 35 wt. %, less than 32.5 wt. %, or less than 30 wt. %. In terms of lower limits, the recycled stream may comprise greater than 0 wt. % high-boiling components, e.g., greater than 5 wt. %, greater than 10 wt. %, greater than 15 wt. %, or greater than 20 wt. %.

In some aspects, the recycle step controls the concentration of heavies in the target. For example, the recycle step may control the concentration of the heavies in the flasher overhead stream by recycling a stream containing heavies to the flasher stream.

In one embodiment, due to the recycling, the recycle step controls the concentration of heavies in the target to be from 0 wt. % to 10 wt. %, e.g., from 0 wt. % to 9 wt. %, from 0 wt. % to 8 wt. %, from 0 wt. % to 7 wt. %, from 1 wt. % to 10 wt. %, from 1 wt. % to 9 wt. %, from 1 wt. % to 8 wt. %, from 1 wt. % to 7 wt. %, from 2 wt. % to 10 wt. %, from 2 wt. % to 9 wt. %, from 2 wt. % to 8 wt. %, from 2 wt. % to 7 wt. %, from 3 wt. % to 10 wt. %, from 3 wt. % to 9 wt. %, from 3 wt. % to 8 wt. %, or from 3 wt. % to 7 wt. %. In terms of upper limits, the recycle step may control the concentration of heavies in the target to be less than 10 wt. %, e.g., less than 9 wt. %, less than 8 wt. %, or less than 7 wt. %. In terms of lower limits, the recycle step may control the concentration of heavies in the target to be greater than 0 wt. %, e.g., greater than 1 wt. %, greater than 2 wt. %, or greater than 3 wt. %.

Exemplary separation and/or purification schemes are disclosed in U.S. Provisional Pat. No. 62/852,604, filed on May 24, 2019, the contents of which are incorporated by reference herein.

Configurations

FIGS. 1-5 show schematic overviews of several configurations of the TCH purification processes disclosed herein.

FIG. 1 shows one embodiment of the adiponitrile separation process 100. In this embodiment, an adiponitrile process stream 101 is separated in a flash evaporator 102 to form a first overhead stream 103 and a first bottoms stream 104. The first overhead stream 103 is then separated in a first distillation column 105 to form a lights stream as a second overhead stream 106 and a second bottoms stream 107. The second bottoms stream is then separated in a second distillation column 108 to form a heavies stream as a third bottoms stream 109 and a TCH stream as a third overhead stream 110. This embodiment also features an optional recycle step 111, whereby a portion of the third bottoms stream 109 is recycled to the first overhead stream 103 and/or the second bottoms stream 107.

Figure 2:
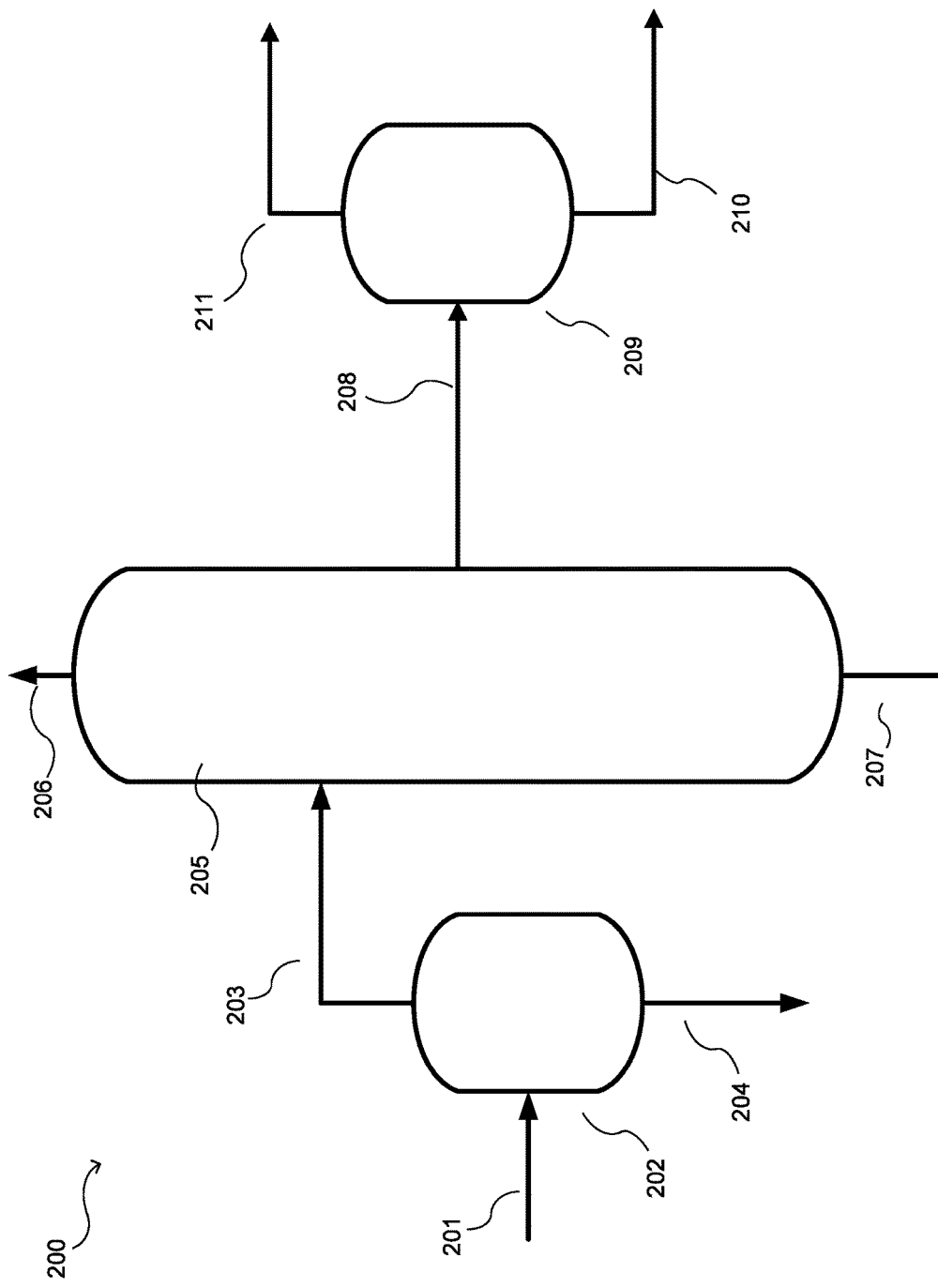
FIG. 2 depicts a schematic overview of another embodiment of the process for producing an intermediate adiponitrile stream.

FIG. 2 shows another embodiment of the adiponitrile separation process 200. In this embodiment, an adiponitrile process stream 201 is separated in a flash evaporator 202 to form a first overhead stream 203 and a first bottoms stream 204. The first overhead stream 203 is then separated in a first distillation column 205 to form a lights stream as a second overhead stream 206, a second bottoms stream 207, and a side draw 208. The side draw 208 is then separated in separated in a flasher 209 to form a TCH stream as a third bottoms stream 210 and a third overhead stream 211.

Figure 3:
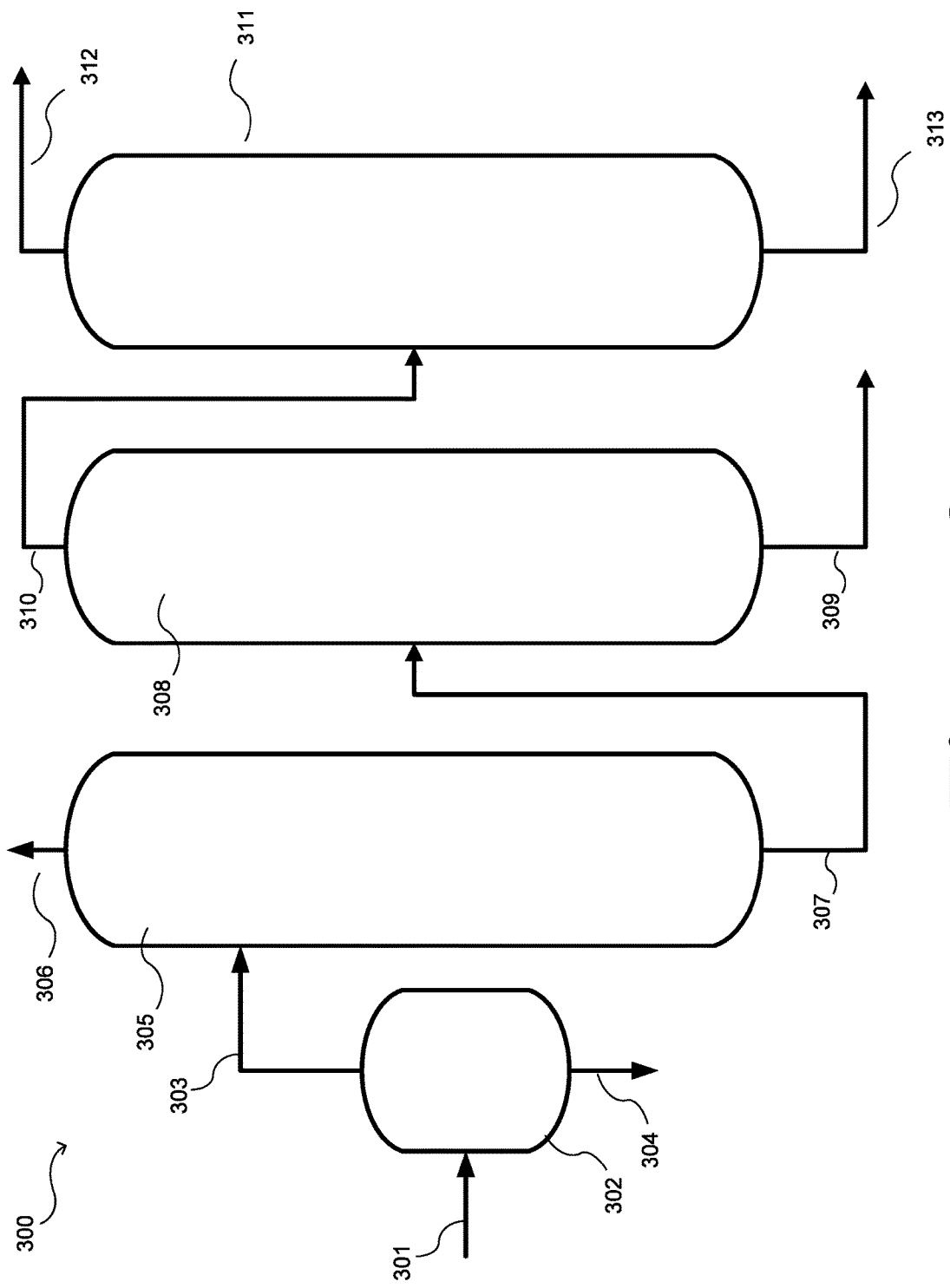
FIG. 3 depicts a schematic overview of another embodiment of the process for producing an intermediate adiponitrile stream.

FIG. 3 shows another embodiment of the adiponitrile separation process 300. In this embodiment, an adiponitrile process stream 301 is separated in a flash evaporator 302 to form a first overhead stream 303 and a first bottoms stream 304. The first overhead stream 303 is then separated in a first distillation column 305 to form a lights stream as a second overhead stream 306 and a second bottoms stream 307. The second bottoms stream 307 is then separated in a second distillation column 308 to form a heavies stream as a third bottoms stream 309 and a third overhead, or distillate, stream 310. The third overhead stream 310 is then separated in a third distillation column 311 to form a fourth overhead stream 312 and a TCH stream as a fourth bottoms stream 313.

Figure 4:
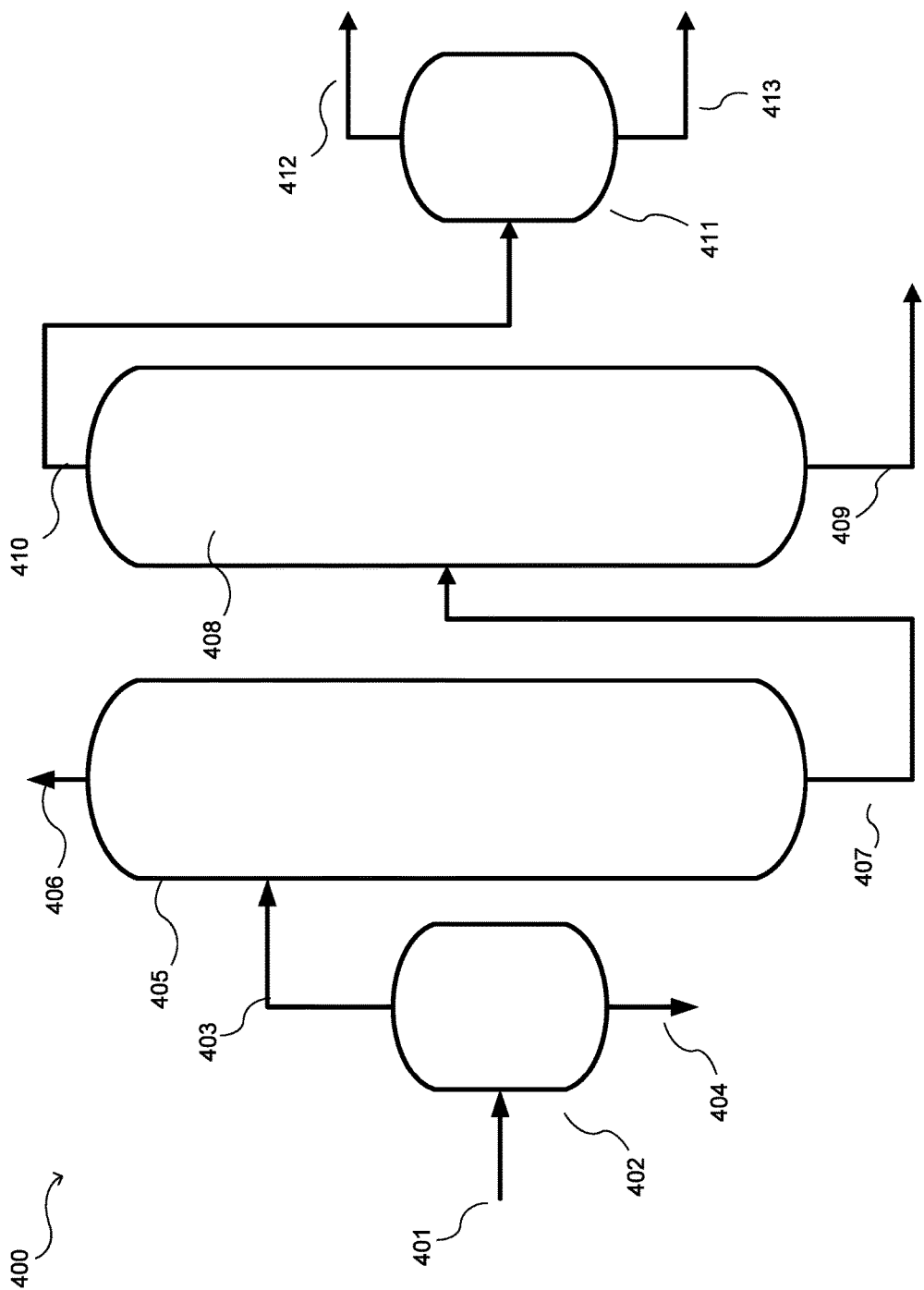
FIG. 4 depicts a schematic overview of another embodiment of the process for producing an intermediate adiponitrile stream.

FIG. 4 shows another embodiment of the adiponitrile separation process 400. In this embodiment, an adiponitrile process stream 401 is separated in a flash evaporator 402 to form a first overhead stream 403 and a first bottoms stream 404. The first overhead stream 403 is then separated in a first distillation column 405 to form a lights stream as a second overhead stream 406 and a second bottoms stream 407. The second bottoms stream 407 is then separated in a second distillation column 408 to form a heavies stream as a third bottoms stream 409 and a third overhead, or distillate, stream 410. The third overhead stream 410 is then separated in a flasher 411 to form a fourth overhead stream 412 and a TCH stream as a fourth bottoms stream 413.

FIG. 5 shows another embodiment of the adiponitrile separation process 500. In this embodiment, an adiponitrile process stream 501 is separated in a flash evaporator 502 to form a first overhead stream 503 and a first bottoms stream 504. The first overhead stream 503 is then separated in a first distillation column 505 to form a lights stream as a second overhead stream 506 and a second bottoms stream 507. The second bottoms stream 507 is then separated in a second distillation column 508 to form a heavies stream as a third bottoms stream 509 and a TCH stream as a third overhead stream 510. This embodiment also features an optional recycle step 511, whereby a portion of the third bottoms stream 509 is recycled to the first overhead stream 503 and/or the second bottoms stream 507. This embodiment also features a treating step 512, whereby the TCH stream 510 is subjected to further treatment to yield a purified TCH stream 513.

The present disclosure will be further understood by reference to the following non-limiting example.

EXAMPLES

For Examples 1 and 2, an adiponitrile process stream was collected from an adiponitrile production and purification process. The adiponitrile process streams of Examples 1 and 2 were fed to a separation process as described herein, e.g., similar to the separation described in FIG. 1.

The adiponitrile process streams were separated in a wiped film evaporator multiple times times, e.g., two or four times. The multiple passes through the wiped film evaporator produced an overhead (first overhead lights stream) and first bottoms heavies stream, which comprised high-boiling components and solid impurities. The first bottoms heavies stream was discarded. The compositions of the first overhead lights stream and the first bottoms stream are provided in Table 1. TCH content, in some cases, included TCH and isomers thereof.

TABLE 1

| | First Separating Step Flash | | |
|---|---|---|---|
| | First Overhead | First Bottoms Stream | |
| Component | Lights Stream | Ex. 1 | Ex. 2 |
| Adiponitrile | 5.0 | 1.0 | 0.7 |
| TCH | 80.0 | 95.0 | 95.9 |
| Lights | 5.0 | 1.5 | 1.8 |
| Heavies | 10.0 | 2.5 | 2.4 |

The first overhead lights stream was distilled in a first distillation column. The first distillation column was operated at a column bottom temperature of about 255° C., and at 1 mmHg and the residence time of the first overhead lights stream in the first distillation column was less than 4 hours. The first distillation column produced a second overhead lights stream. The first distillation column also produced an intermediate bottoms stream, which contained a high concentration of TCH and some heavies.

The first overhead lights streams of Examples 1 and/or 2 were distilled in a first distillation column. The first distillation column was operated at a column bottom (reboiler) temperature of about 255° C., an operating pressure of about 1 mmHg, and the residence time of the first overhead lights stream in the first distillation column was less than 4 hours. The first distillation column produced a second overhead lights stream. Samples of this stream were collected at various times and analyzed. Compositions of these samples are shown in Table 2a. In some cases, the number of cycles in the wiped film evaporator was found to affect the composition of the resulting overhead.

TABLE 2a

| | Second Separating Step (First Column) | | |
|---|---|---|---|
| | Second Intermediate Adiponitrile Stream | | |
| Component | Sam. 1 | Sam. 2 | Sam. 3 |
| Adiponitrile | 7.1 | 27.09 | 8.93 |
| TCH | 80.3 | 45.77 | 70.49 |
| Lights | 10.6 | 24.59 | 18.97 |
| Heavies | 2.0 | 2.54 | 2.27 |

The first distillation column also produced a second bottoms stream, which contained a high concentration of TCH and some heavies. Samples of this stream were collected at various times and analyzed. Compositions of these samples are shown in Table 2b.

TABLE 2b

Second Separating Step (First Column)

Second Bottoms Stream

| Comp. | Sam. 4 | Sam. 5 | Sam. 6 | Sam. 7 | Sam. 8 | Sam. 9 | Sam. 10 | Sam. 11 | Sam. 12 | Sam. 13 | Sam. 14 |
|---|---|---|---|---|---|---|---|---|---|---|---|
| Adipo | 0.0 | 0.009 | 0 | 0 | 0.003 | 0.006 | 0.004 | 0 | 0 | 0 | 0 |
| TCH | 97.4 | 97.57 | 96.21 | 97.24 | 97.5 | 97.4 | 97.4 | 97.3 | 97.8 | 97.7 | 98.1 |
| Lights | 0.0 | 0.21 | 0.04 | 0.14 | 0.19 | 0.09 | 0.1 | 0.11 | 0.05 | 0.00 | 0.03 |
| Heavies | 2.6 | 2.2 | 3.75 | 2.62 | 2.30 | 2.53 | 2.53 | 2.48 | 2.18 | 2.34 | 1.9 |

The second bottoms streams were then distilled in a second distillation column. The second distillation column was operated at a column bottom (reboiler) temperature of about 263° C., an operating pressure of about 1 mmHg, and the residence time of the second bottoms stream in the second distillation column was less than 4 hours. The second distillation column produced a third bottoms stream (heavies stream). The heavies stream can be recycled and/or discarded. The second distillation column also produced a third overhead stream (TCH stream). Samples of these streams were collected at various times and analyzed. Compositions of these samples are shown in Tables 3a-3d.

TABLE 3a

Second Separating Step (Second Column)

TCH Stream

| Component | Sam. 15 | Sam. 16 | Sam. 17 | Sam. 18 | Sam. 19 | Sam. 20 | Sam. 21 | Sam. 22 |
|---|---|---|---|---|---|---|---|---|
| Adiponitrile | 0.108 | 0.071 | 0.129 | 0.045 | 0.051 | 0.12 | 0.05 | 0.02 |
| TCH | 98.88 | 98.95 | 98.77 | 97.0 | 97.72 | 98.18 | 99.21 | 99.0 |
| Lights | 0.34 | 0.27 | 0.29 | 0.30 | 0.29 | 0.34 | 0.23 | 0.08 |
| Heavies | 0.67 | 0.67 | 0.81 | 2.61 | 1.89 | 1.34 | 0.51 | 0.89 |

TABLE 3b

Second Separating Step (Second Column)

TCH Stream

| Component | Sam. 22 | Sam. 23 | Sam. 24 | Sam. 25 | Sam. 26 | Sam. 27 | Sam. 28 | Sam. 29 |
|---|---|---|---|---|---|---|---|---|
| Adiponitrile | 0.046 | 0.026 | 0.021 | 0.016 | 0.03 | 0.02 | 0.038 | 0.023 |
| TCH | 99.12 | 99.06 | 99.03 | 99.65 | 99.03 | 99.28 | 99.34 | 99.48 |
| Lights | 0.46 | 0.14 | 0.08 | 0.11 | 0.22 | 0.16 | 0.12 | 0.19 |
| Heavies | 0.38 | 0.77 | 0.87 | 0.22 | 0.72 | 0.55 | 0.53 | 0.30 |

TABLE 3c

Second Separating Step (Second Column)

Heavies Stream

| Component | Sam. 30 | Sam. 31 | Sam. 32 | Sam. 33 | Sam. 34 | Sam. 35 | Sam. 36 | Sam. 37 |
|---|---|---|---|---|---|---|---|---|
| Adiponitrile | 0 | 0 | 0 | 0 | 0 | 0 | 0 | 0 |
| TCH | 90.92 | 95.36 | 93.08 | 95.0 | 94.29 | 94.52 | 97.32 | 97.23 |
| Lights | 0.07 | 0.06 | 0.11 | 0.11 | 0.07 | 0.02 | 0.11 | 0.07 |
| Heavies | 9.01 | 4.55 | 6.81 | 4.9 | 5.63 | 5.46 | 2.48 | 2.7 |

TABLE 3d

| | Second Separating Step (Second Column) | | | | | | |
|---|---|---|---|---|---|---|---|
| | Heavies Stream | | | | | | |
| Component | Sam. 38 | Sam. 39 | Sam. 40 | Sam. 41 | Sam. 42 | Sam. 43 | Sam. 44 |
| Adiponitrile | 0 | 0 | 0 | 0 | 0 | 0 | 0 |
| TCH | 94.99 | 92.43 | 91.76 | 89.65 | 90.27 | 88.56 | 95.06 |
| Lights | 0.09 | 0 | 0 | 0 | 0 | 0 | 0 |
| Heavies | 4.91 | 7.56 | 8.24 | 10.35 | 9.73 | 11.44 | 4.94 |

As the above tables show, the purification process carried out in Examples 1 and 2, with low column pressure and high reboiler temperature, e.g., less than 11 mm Hg and greater than 235° C., produced a highly pure TCH stream. In particular, the purification process resulted in a TCH stream comprising greater than 97 wt. % TCH, e.g., in most cases greater than 99 wt. %, and comprising little or no measurable adiponitrile or lights. As shown, the concentration of the heavies in the intermediate bottoms stream and/or the second bottoms heavies stream was maintained within the ranges and limits disclosed herein.

As shown, it was unexpectedly found that as the feed to the column(s) has a higher adiponitrile concentration, the concentration improvement in the column overhead is surprisingly improved. In simulations using similar equipment, when adiponitrile concentration in the column feed was above 10 wt %, then the adipo concentration in the overhead was advantageously higher, e.g., over 50%.

Embodiments

As used below, any reference to a series of embodiments is to be understood as a reference to each of those embodiments disjunctively (e.g., "Embodiments 1-4" is to be understood as "Embodiments 1, 2, 3, or 4").

Embodiment 1 is a process for purifying tricyanohexane (TCH), the process comprising: a) separating an adiponitrile process stream comprising adiponitrile and TCH to form a first overhead lights stream comprising low-boiling components and high-boiling components and a first bottoms heavies stream comprising high-boiling components and solid impurities; and b) separating the first overhead lights stream in one or more distillation columns to form a second overhead lights stream comprising low-boiling components, a second bottoms heavies stream comprising high-boiling components, and a TCH stream comprising TCH and less than 10 wt. % impurities; wherein the distillation column is a low pressure distillation column.

Embodiment 2 is the process of embodiment 1, wherein the low pressure distillation column is operated under vacuum.

Embodiment 3 is the process of embodiment(s) 1-2, wherein the low pressure distillation column is operated with a column top pressure less than 100 mm Hg.

Embodiment 4 is the process of embodiment(s) 1-3, wherein the low pressure distillation column is operated with a column bottom pressure less than 100 mm Hg.

Embodiment 5 is the process of embodiment(s) 1-4, wherein the distillation column comprises a reboiler, and the reboiler is operated at a temperature greater than 250° C.

Embodiment 6 is the process of embodiment(s) 1-5, wherein the distillation column comprises a reboiler, and the reboiler utilizes a hot oil system Embodiment 7 is the process of embodiment(s) 1-6, wherein step a) comprises flashing the adiponitrile process stream, treating the adiponitrile process stream in a wiped film evaporator, and/or treating the adiponitrile process stream in a falling film evaporator.

Embodiment 8 is the process of embodiment(s) 1-7, wherein step a) is carried out at a temperature of at least 250° C.

Embodiment 9 is the process of embodiment(s) 1-8, wherein the TCH stream comprises less than 1 wt. % impurities.

Embodiment 10 is the process of embodiment(s) 1-9, wherein the first overhead lights stream comprises from 0 wt. % to 20 wt. % heavies.

Embodiment 11 is the process of embodiment(s) 1-10, further comprising recycling at least a portion of the second bottoms heavies stream, optionally comprising from 0 wt. % to 40 wt. % high-boiling components.

Embodiment 12 is the process of embodiment(s) 1-11, wherein step b) further comprises: separating the first overhead lights stream in a first distillation column to form the second overhead lights stream and the second bottoms heavies stream; and separating the second bottoms heavies stream in a second distillation column to form a third bottoms heavies stream and a third overhead TCH stream.

Embodiment 13 is the process of embodiment(s) 12, further comprising recycling at least a portion of the third bottoms heavies stream to the second bottoms heavies stream and/or to the first overhead lights stream.

Embodiment 14 is the process of embodiment(s) 1-13, further comprising a treating step of treating the TCH stream to form a purified TCH stream.

Embodiment 15 is the process of embodiment(s) 14, wherein the treating step comprises nitrogen stripping or treating with a molecular sieve.

Embodiment 16 is the process of embodiment(s) 14-15, wherein the purified TCH stream comprises less than 0.1 wt. % impurities, less than 20 ppm water, and/or less than 5 ppm metals.

Embodiment 17 is the process of embodiment(s) 1-16, wherein the adiponitrile process stream is a co-product stream produced by an adiponitrile production and/or an adiponitrile purification process.

Embodiment 18 is the process of embodiment(s) 17, wherein the first bottoms heavies stream and/or the second overhead lights stream is recycled to the adiponitrile production and/or the adiponitrile purification process.

Embodiment 19 is a process for purifying TCH, the process comprising: a) separating an adiponitrile process stream comprising adiponitrile and TCH to form a first overhead lights stream comprising low-boiling components and high-boiling components, and a first bottoms heavies stream comprising high-boiling components and solid impurities; b) separating the first overhead lights stream to form a second overhead lights stream comprising low-boiling components, and a second bottoms heavies stream comprising TCH and heavies; c) distilling the second bottoms heavies stream to form a third overhead lights stream comprising TCH and less than 5 wt,% impurities, and a third bottoms heavies stream comprising heavies; wherein step b) or step c) comprises distilling in a low pressure distillation column.

Embodiment 20 is the process of embodiment(s) 19, wherein the low pressure distillation column comprises a reboiler, and the reboiler is operated at a temperature greater than 250° C.

Embodiment 21 is a process for purifying TCH, the process comprising a) separating an adiponitrile process stream comprising adiponitrile and TCH to form a first overhead lights stream comprising low-boiling components and high-boiling components, and a first bottoms heavies stream comprising high-boiling components and solid impurities; b) distilling the first overhead lights stream to form a second overhead lights stream comprising low-boiling components, a second bottoms heavies stream comprising heavies, and a side draw comprising TCH and lights; c) separating the side draw in a second flash vessel to form a third bottoms heavies stream comprising TCH and less than 5 wt. % impurities wherein step b) or step c) comprises distilling in a low pressure distillation column.

Embodiment 22 is the process of embodiment(s) 21, wherein the low pressure distillation column comprises a reboiler, and the reboiler is operated at a temperature greater than 250° C.

Embodiment 23 is a process for purifying TCH, the process comprising: a) separating an adiponitrile process stream to form a first overhead lights stream comprising low-boiling components and high-boiling components, and a first bottoms heavies stream comprising high-boiling components and solid impurities; b) distilling the first overhead lights stream to form a second overhead lights stream comprising low-boiling components, and a second bottoms heavies stream comprising TCH and heavies; c) distilling the second bottoms heavies stream to form a third distillate comprising TCH and impurities, and a third bottoms heavies stream comprising heavies; and d) distilling the third distillate to form a fourth overhead lights stream comprising low-boiling components, and a fourth bottoms heavies stream comprising TCH and less than 5 wt. % impurities wherein the step b), step c), or step d) comprises distilling in a low pressure distillation column.

Embodiment 24 is the process of embodiment(s) 23, wherein the low pressure distillation column comprises a reboiler, and the reboiler is operated at a temperature greater than 250° C.

Embodiment 25 is a process for purifying TCH, the process comprising: a) separating an adiponitrile process stream to form a first overhead lights stream comprising low-boiling components and high-boiling components, and a first bottoms heavies stream comprising high-boiling components and solid impurities; b) distilling the first overhead lights stream to form a second overhead lights stream comprising low-boiling components, and a second bottoms heavies stream comprising TCH and heavies; c) distilling the second bottoms heavies stream to form a third distillate comprising TCH and impurities, and a third bottoms heavies stream comprising heavies; and d) separating the third distillate in a second flash vessel to form a fourth overhead lights stream comprising low-boiling components, and a fourth bottoms heavies stream comprising TCH and less than 5 wt. % impurities wherein step b), step c), or step d) comprises distilling in a low pressure distillation column.

Embodiment 26 is the process of embodiment(s) 25, wherein the low pressure distillation column comprises a reboiler, and the reboiler is operated at a temperature greater than 250° C.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit.

We claim:

1. A process for purifying tricyanohexane (TCH), the process comprising:
   a) separating an adiponitrile process stream comprising adiponitrile and TCH by flashing the adiponitrile process stream, treating the adiponitrile process stream in a wiped film evaporator, and/or treating the adiponitrile process stream in a falling film evaporator to form a first overhead lights stream comprising low-boiling components and high-boiling components and a first bottoms heavies stream comprising high-boiling components and solid impurities; and
   b) separating the first overhead lights stream in one or more distillation columns to form a second overhead lights stream comprising low-boiling components, a heavies stream comprising high-boiling components, and a TCH stream comprising TCH and less than 10 wt. % impurities;
   wherein the one or more distillation columns are operated at low pressure.

2. The process of claim 1, wherein the one or more distillation columns are operated under vacuum.

3. The process of claim 1, wherein the one or more distillation columns are operated with a column top pressure less than 100 mm Hg.

4. The process of claim 1, wherein the one or more distillation columns are operated with a column bottom pressure less than 100 mm Hg.

5. The process of claim 1, wherein the one or more distillation columns comprise a reboiler and the reboiler is operated at a temperature greater than 250° C.

6. The process of claim 1, wherein the one or more distillation columns comprise a reboiler and the reboiler utilizes a hot oil system.

7. The process of claim 1, wherein step a) is carried out at a temperature of at least 250° C.

8. The process of claim 1, wherein the TCH stream comprises less than 1 wt. % impurities.

9. The process of claim 1, further comprising recycling at least a portion of the bottoms heavies stream produced in step b), comprising from 5 wt. % to 40 wt. % high-boiling components.

10. The process of claim 1, wherein step b) further comprises:
- separating the first overhead lights stream in a first distillation column to form the second overhead lights stream and a second bottoms heavies stream; and
- separating the second bottoms heavies stream in a second distillation column to form a third bottoms heavies stream and a third overhead stream comprising TCH.

11. The process of claim 10, further comprising recycling at least a portion of the third bottoms heavies stream to the second bottoms heavies stream and/or to the first overhead lights stream.

12. The process of claim 1, wherein the purified TCH stream comprises less than 0.1 wt. % impurities, less than 20 ppm water, and/or less than 5 ppm metals.

13. The process of claim 1, wherein the adiponitrile process stream is a co-product stream produced by an adiponitrile production and/or an adiponitrile purification process.

14. The process of claim 13, wherein the first bottoms heavies stream and/or the second overhead lights stream is recycled to the adiponitrile process stream.

15. A process for purifying TCH, the process comprising:
a) separating an adiponitrile process stream comprising adiponitrile and TCH by flashing the adiponitrile process stream, treating the adiponitrile process stream in a wiped film evaporator, and/or treating the adiponitrile process stream in a falling film evaporator to form a first overhead lights stream comprising low-boiling components and high-boiling components, and a first bottoms heavies stream comprising high-boiling components and solid impurities;
b) separating the first overhead lights stream to form a second overhead lights stream comprising low-boiling components, and a second bottoms heavies stream comprising TCH and heavies;
c) distilling the second bottoms heavies stream to form a third overhead lights stream comprising TCH and less than 5 wt. % impurities, and a third bottoms heavies stream comprising heavies;
wherein step b) or step c) comprises distilling in a low pressure distillation column.

16. A process for purifying TCH, the process comprising:
a) separating an adiponitrile process stream comprising adiponitrile and TCH to form a first overhead lights stream comprising low-boiling components and high-boiling components, and a first bottoms heavies stream comprising high-boiling components and solid impurities;
b) distilling the first overhead lights stream to form a second overhead lights stream comprising low-boiling components, a second bottoms heavies stream comprising heavies, and a side draw comprising TCH and lights;
c) separating the side draw in a flash vessel to form a third bottoms heavies stream comprising TCH and less than 5 wt. % impurities wherein step b) comprises distilling in a low pressure distillation column.

17. A process for purifying TCH, the process comprising:
a) separating an adiponitrile process stream by flashing the adiponitrile process stream, treating the adiponitrile process stream in a wiped film evaporator, and/or treating the adiponitrile process stream in a falling film evaporator to form a first overhead lights stream comprising low-boiling components and high-boiling components, and a first bottoms heavies stream comprising high-boiling components and solid impurities;
b) distilling the first overhead lights stream to form a second overhead lights stream comprising low-boiling components, and a second bottoms heavies stream comprising TCH and heavies;
c) distilling the second bottoms heavies stream to form a third distillate comprising TCH and impurities, and a third bottoms heavies stream comprising heavies; and
d) distilling the third distillate to form a fourth overhead lights stream comprising low-boiling components, and a fourth bottoms heavies stream comprising TCH and less than 5 wt. % impurities;
wherein the step b), step c), or step d) comprises distilling in a low pressure distillation column.

18. A process for purifying TCH, the process comprising:
a) separating an adiponitrile process stream to form a first overhead lights stream comprising low-boiling components and high-boiling components, and a first bottoms heavies stream comprising high-boiling components and solid impurities;
b) distilling the first overhead lights stream to form a second overhead lights stream comprising low-boiling components, and a second bottoms heavies stream comprising TCH and heavies;
c) distilling the second bottoms heavies stream to form a third distillate comprising TCH and impurities, and a third bottoms heavies stream comprising heavies; and
d) separating the third distillate in a flash vessel to form a fourth overhead lights stream comprising low-boiling components, and a fourth bottoms heavies stream comprising TCH and less than 5 wt. % impurities;
wherein step b) or step c) comprises distilling in a low pressure distillation column.

* * * * *